United States Patent
Takahashi et al.

(10) Patent No.: US 8,436,292 B2
(45) Date of Patent: May 7, 2013

(54) LUBRICANT DETERIORATION DETECTION DEVICE WITH A PLURALITY OF LIGHT DETECTORS, A PLURALITY OF LIGHT GUIDE ELEMENTS OF DIFFERENT LENGTHS AND A LINEAR LIGHT SOURCE

(75) Inventors: Toru Takahashi, Iwata (JP); Akio Nakajima, Iwata (JP)

(73) Assignee: NTN Corporation, Osaka (JP)

( * ) Notice: Subject to any disclaimer, the term of this patent is extended or adjusted under 35 U.S.C. 154(b) by 383 days.

(21) Appl. No.: 12/162,294

(22) PCT Filed: Jan. 26, 2007

(86) PCT No.: PCT/JP2007/000031
§ 371 (c)(1),
(2), (4) Date: Jul. 25, 2008

(87) PCT Pub. No.: WO2007/088701
PCT Pub. Date: Aug. 9, 2007

(65) Prior Publication Data
US 2009/0050827 A1 Feb. 26, 2009

(30) Foreign Application Priority Data

| Feb. 1, 2006 | (JP) | 2006-024127 |
| Feb. 7, 2006 | (JP) | 2006-029337 |
| Feb. 7, 2006 | (JP) | 2006-029338 |
| Feb. 15, 2006 | (JP) | 2006-037546 |
| Feb. 20, 2006 | (JP) | 2006-042378 |

(51) Int. Cl.
*G02B 6/42* (2006.01)
*G01N 21/49* (2006.01)

(52) U.S. Cl.
USPC ..................... 250/227.25; 250/573

(58) Field of Classification Search .......... 250/573–577, 250/578.1, 227.11, 227.25, 216, 221, 239, 250/222.2; 340/555, 540, 556, 557, 600, 340/603–619; 356/337–343
See application file for complete search history.

(56) References Cited

U.S. PATENT DOCUMENTS 3,548,657 A * 12/1970 Panerai et al. .................. 73/293
4,080,076 A    3/1978 Carr
(Continued)

FOREIGN PATENT DOCUMENTS

| JP | 56-153238 | 11/1981 |
| JP | 62-6524 | 2/1987 |

(Continued)

OTHER PUBLICATIONS

International Preliminary Report and Written Opinion dated Aug. 14, 2008 issued in corresponding International Application No. PCT/JP2007/000031, 8 pages.

(Continued)

*Primary Examiner* — Que T Le
*Assistant Examiner* — Jennifer Bennett
(74) *Attorney, Agent, or Firm* — Osha Liang LLP

(57) ABSTRACT

To provide a lubricant deterioration detecting device having a high degree of freedom in arranging within the bearing assembly or the like and capable of stably detecting the status of deterioration of the lubricant without being affected by the thickness of the lubricant and a change in temperature and also to provide a detector incorporated bearing assembly equipped with such lubricant deterioration detecting device, the lubricant deterioration detecting device includes a light source, a plurality of light detecting components for detecting rays of light emitted from the light source and subsequently transmitted through a lubricant, and a determining unit. The plural light detecting components have respective light detecting faces sequentially displaced in position. The determining unit compares respective signal strengths of outputs from the plural light detecting components to detect the status of deterioration of the lubricant.

17 Claims, 16 Drawing Sheets

U.S. PATENT DOCUMENTS

| | | | |
|---|---|---|---|
| 4,087,184 A * | 5/1978 | Knapp et al. | 356/427 |
| 4,265,535 A * | 5/1981 | Pitt | 356/70 |
| 4,277,681 A | 7/1981 | Borken | |
| 5,446,531 A | 8/1995 | Boyer et al. | |
| 5,772,606 A | 6/1998 | Ashibe et al. | |
| 6,315,955 B1 * | 11/2001 | Klein | 422/73 |
| 2005/0088646 A1 | 4/2005 | Kong et al. | |

FOREIGN PATENT DOCUMENTS

| | | |
|---|---|---|
| JP | 63-26557 | 2/1988 |
| JP | 1-272941 | 10/1989 |
| JP | 07-294520 | 11/1995 |
| JP | 10-26584 | 1/1998 |
| JP | 10026584 A * | 1/1998 |
| JP | 10-281986 | 10/1998 |
| JP | 10-318920 | 12/1998 |
| JP | 2003-139696 | 5/2003 |
| JP | 2003-166696 | 6/2003 |
| JP | 2003166696 A * | 6/2003 |
| JP | 2004-293776 | 10/2004 |
| JP | 2004-309296 | 11/2004 |
| JP | 2004-340806 | 12/2004 |
| JP | 2004340806 A * | 12/2004 |
| JP | 2006-502387 | 1/2006 |
| WO | WO-2004/031752 | 4/2004 |

OTHER PUBLICATIONS

International Search Report (English & Japanese) for PCT/JP2007/000031 mailed Feb. 13, 2007 (6 pages).

Patent Abstracts of Japan 2004-340806 dated Dec. 2, 2004 (1 page).
Patent Abstracts of Japan 10-026584 dated Jan. 27, 1998 (1 page).
Patent Abstracts of Japan 10-281986 dated Oct. 23, 1998 (1 page).
Patent Abstracts of Japan 01-272941 dated Oct. 31, 1989 (1 page).
Patent Abstracts of Japan 2003-166696 dated Jun. 13, 2003 (1 page).
Patent Abstracts of Japan 2003-139696 dated May 14, 2003 (1 page).
Patent Abstracts of Japan 63-026557 dated Feb. 4, 1988 (1 page).
Patent Abstracts of Japan 2004-293776 dated Oct. 21, 2004 (1 page).
European Search Report for related Patent Application No. 07706283.4 dated May 6, 2010, (3 pages).
Patent Abstracts of Japan for patent application with Publication No. 56-153238, Publication Date : Nov. 11, 1981, (1 page).
Patent Abstracts of Japan for patent application with Publication No. 10-318920, Publication Date : Dec. 4, 1998, (1 page).
Patent Abstracts of Japan for patent application with Publication No. 2004-309296, Publication Date : Nov. 4, 2004, (1 page).
Patent Abstracts of Japan for patent application with Publication No. 07-294520, Publication Date : Nov. 10, 1995, (1 page).
Communication pursuant to Article 94(3) EPC for related Patent Application No. 07706283.4 dated May 26, 2010, (8 pages).
Office Action for Japanese Patent Application No. 2006-024127 Dated Jul. 5, 2011 (6 Pages w/ English Translation).
Office Action issued in Japan Application No. 2006-037546, Dated Aug. 23, 2011 (6 Pages with English Translation).

* cited by examiner

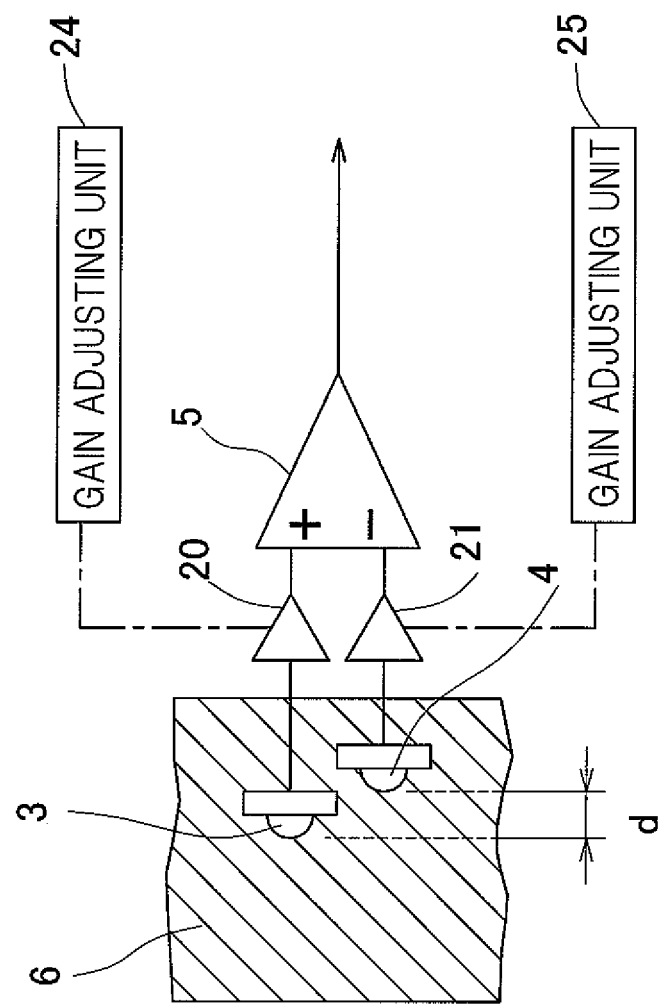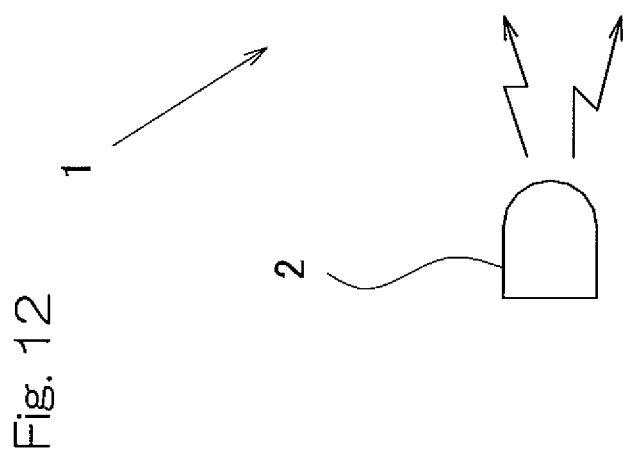
Fig. 12

(PRIOR ART)

LUBRICANT DETERIORATION DETECTION DEVICE WITH A PLURALITY OF LIGHT DETECTORS, A PLURALITY OF LIGHT GUIDE ELEMENTS OF DIFFERENT LENGTHS AND A LINEAR LIGHT SOURCE

BACKGROUND OF THE INVENTION

1. Field of the Invention

The present invention relates to a lubricant deterioration detecting device for detecting the status of deterioration of a lubricant resulting from admixture of an alien substance and also to a detecting device incorporated bearing assembly equipped with such lubricant detection detecting device such as, for example, a detector incorporated bearing assembly for use in railway vehicles, automotive vehicles and industrial machines or the like.

2. Description of the Prior Art

In the bearing assembly filled with a lubricant, an insufficient lubrication occurs once the lubricant (such as, for example, a grease or oil) within the bearing assembly is deteriorated, resulting in a reduction in lifetime of the bearing assembly. Since determination of the occurrence of the insufficient lubrication in reference to the status of vibration or the like occurring in the bearing assembly is carried out when and after an operating abnormality has occurred as a result of expiration of the lifetime of the bearing assembly, the presence or absence of an abnormality in lubrication cannot be carried out at an early time. In view of this, it has been desired to monitor the status of the lubricant within the bearing assembly regularly or in real time so that the occurrence of the abnormality and/or the time for maintenance can be predicated.

A major cause of deterioration of the lubricant may include an admixture of powdery wear debris, which is produced as the bearing assembly is used, into the lubricant.

For detecting the status of wear of the bearing assembly, a sensor incorporated bearing assembly has been suggested, in which a sensor in the form of an electrode or a coil is arranged inside a sealing member of the bearing assembly so that the electrical characteristic of the lubricant resulting from the admixture of the wear debris can be detected. (See, for example, the Japanese Laid-open Patent Publication No. 2004-293776, published Oct. 21, 2004.)

However, since the sensor incorporated bearing assembly disclosed in the above mentioned patent document is so designed that the electrical characteristic of the lubricant can be detected, no change in characteristic can be detected unless a condition is established in which conduction occurs as a result of inclusion of a substantial amount of wear debris, and thus, difficulty often occurs in detecting the inclusion of the alien substance.

In order to alleviate the problems discussed above, such an optical construction, although it has not yet been known, has been contemplated, in which, for example, as shown in FIG. 25, an light emitting element 53 and a light receiving element 54 are arranged, with a lubricant 55 intervening therebetween, so that the status of deterioration of the lubricant 55 can be estimated from the intensity of light emitted from the light emitting element 53 and subsequently detected by the light receiving element 54.

In the case of the above described construction, it has been found that where the thickness d of the lubricant 55 forming an object to be detected changes as shown by the broken line in FIG. 25, the intensity of light detected by the light receiving element 54 changes correspondingly, and any provision is therefore needed to maintain the thickness d of the lubricant 55 at a constant value.

In view of the above, such an alternative construction, although it has also not yet been known, has been contemplated, in which, for example, as shown in FIG. 26, one end of an optical fiber 56 on a light emitting side and one end of an optical fiber 57 on a light receiving side are so arranged as to oppose to each other with the lubricant 55 intervening therebetween and the light emitting element 53 and the light receiving element 54 are arranged in proximity to the other ends of the optical fibers 56 and 57 on the light emitting and receiving sides, respectively.

With the construction shown in FIG. 26, rays of light emitted from the light emitting element 53 are transmitted across the lubricant 55, positioned at a measuring site 58, through the light emitting optical fiber 56 and are subsequently detected by the light receiving element 54 through the light receiving optical fiber 57, whereby the amount of foreign matter admixed in the lubricant 55 can be estimated from the intensity of the transmitted light detected by the light receiving element 54. In this case, since the surface area of each of the optical fibers 56 and 57 at the measuring site 58 can be minimized, ingress of the lubricant 55 into the measuring site 58 can be facilitated and the lubricant once entering the measuring site 58 can easily be maintained at a constant thickness.

However, even with the construction shown in FIG. 26, the measuring site 58 requires a vessel of a structure designed to maintain the thickness d of the lubricant 55 at a constant value and, therefore, the freedom of arrangement within, for example, a bearing assembly is lowered particularly where it is used in detecting the status of deterioration of the lubricant of a kind sealed within the bearing assembly.

SUMMARY OF THE INVENTION

An object of the present invention is to provide a lubricant deterioration detecting device having a high degree of freedom in arranging within the bearing assembly or the like and capable of stably detecting the status of deterioration of the lubricant without being affected by the thickness of the lubricant and a change in temperature and also to provide a detecting device incorporated bearing assembly equipped with such lubricant deterioration detecting device.

The lubricant deterioration detecting device of the present invention includes a light source, a plurality of light detecting components for detecting rays of light emitted from the light source and subsequently transmitted through a lubricant, and a determining unit for detecting the status of deterioration of the lubricant. The plural light detecting components have respective light detecting faces sequentially displaced in position, and the determining unit is operable to compare respective signal strengths of outputs from the plural light detecting components.

As described above, since this lubricant deterioration detecting device is so designed that while the plural light detecting components are arranged, for example, in line with their light detecting faces sequentially displaced in position, the status of deterioration of the lubricant can be detected when the signal strengths of the outputs of those light detecting components are compared with each other by the determining unit, the status of deterioration of the lubricant can be detected without being affected by the thickness of the lubricant itself, the intensity of light emitted from the light source and the distance between the light source and the light detecting components, when such detection is made with the plural light detecting components arranged in the lubricant.

As a result, even where the lubricant deterioration detecting device is arranged within the bearing assembly, a large freedom of arrangement is available and construction is possible to accommodate to the limited available space for installation. Considering that the status of deterioration of the lubricant is detected by comparing the respective signal strengths of the outputs of the plural light detecting components, a stable detection can be accomplished without being adversely affected by common mode noises such as a power source variation. Also, arrangement of the light detecting components within the lubricant is effective in that influences brought about by a temperature dependent change in characteristic can be counterbalanced among the plural light detecting components and, accordingly, a highly accurate detection can be accomplished.

In the present invention, the determining unit referred to above may be of a type capable of estimating an amount of the alien substance admixed into the lubricant through comparison of the signal strengths referred to above.

By way of example, where the lubricant is filled within the bearing assembly, foreign matter such as, for example, powdery wear debris is trapped into the lubricant as the bearing assembly is used in practice and, therefore, a detection output of the determining unit becomes low as the amount of the alien substance admixed increases. Accordingly, the amount of the alien substance admixed into the lubricant can be estimated from the value of the detection output of the determining unit. On the other hand, since increase of the amount of the alien substance admixed means a progress of deterioration of the lubricant, the determining unit can detect the status of lubricant from the estimated amount of the alien substance admixed.

In the present invention, each of the light detecting components referred to above may include a detector and a light guide element having one end in the form of a base end connected with the detector and the other end in the form of a free end forming the light detecting face. Since even in this construction, the plural light detecting components have their detecting faces sequentially displaced in position, the status of deterioration of the lubricant can be detected without being affected by the thickness of the lubricant itself, the intensity of the light source and the distance between the light source and the light detecting components.

In the present invention, each of the light detecting components referred to above may include a detector and an optical fiber having one end in the form of a base end connected with the detector and the other end in the form of a free end forming the light detecting face. Where the optical fibers are employed, a detecting site, where the plural light detecting components are arranged, can have a reduced thickness and, therefore, the lubricant can be allowed to enter the detecting site easily and a stable detection can be accomplished accordingly.

In the present invention, the light source may be in the form of a linear-shaped light source. Where the light source is in a line shape, the intensity of light incident on the detecting site comes to be uniform regardless of the position and, therefore, a stable detection is possible.

In the present invention, the determining unit referred to above may be of a type capable of calculating a light transmittance of the lubricant. Since the light transmittance of the lubricant attenuates as the deterioration of the lubricant proceeds accompanied by, for example, an increase of the amount of the alien substance admixed within the lubricant, calculation of the light transmittance of the lubricant can lead to detection of the status of deterioration of the lubricant.

In the present invention, the determining unit includes a selector section for excluding, from the output signals of the plural light detecting components, output signals of a light detecting components which generate a saturated output, and output signals of light detecting components indicative of a detected light intensity not attaining a predetermined value, in order to use respective output signals of the rest of the light detecting components for detection of the status of deterioration of the lubricant.

It may occur that depending on the intensity of light emitted from the light source, some of the light detecting components may generate a saturated output or generate no output. However, even in such case, it is possible to select, by means of the selector section, comparison output of the light detecting components then generating a proper output and then to assuredly detect the status of deterioration of the lubricant from a broad range of locations.

The lubricant deterioration detecting device of the present invention may include two light detecting components of the kind referred to above.

According to the lubricant deterioration detecting device of the construction described above, rays of light from the light source are attenuated before they reach the light detecting components as they are absorbed and/or scattered on the way, and the intensity of such light is detected by the first light detecting components. When using as reference, the output of the second light detecting component to which light arrives first, the output of the second light detecting component is evaluated, it is possible to detect the amount of light attenuated due to the distance between the two light detecting components. In this way, since construction is employed, in which the amount of light attenuated due to the distance between the two light detecting components can be detected, if the spacing between the light detecting components is fixed, measurement, which does not depend on the distance from the light source and the intensity of the light source, can be accomplished. Accordingly, if this output difference is used, estimation of the status of deterioration of the lubricant, for example, the amount of, for example, alien substance, generated as a result of frictional wear, admixed can be estimated without being adversely affected by, for example, the thickness of the lubricant.

Since the distance between the light source and the light detecting components need not be fixed, the degree of freedom of arrangement comes to be high and construction is possible to accommodate to the limited space available for installation. Also, because of the construction in which the signal strengths of the two light detecting components are compared to achieve the detection, a stable detection can be accomplished without adversely affected by common mode noises such as variation in electric power supply. Even though the two light detecting components are arranged within the lubricant, changes in characteristic resulting from change in temperature between the two light detecting components can be counterbalanced and, hence, an accurate detection can be accomplished.

In the present invention, a temperature sensor may be provided at a position in proximity to the light detecting components. In the case of this construction, by allowing the temperature sensor to monitor the temperatures of the lubricant and the light detecting components, correction appropriate to the temperature dependent change can be applied to the detection result. Accordingly, a further accurate detection can be accomplished and the possibility that a change in detected signal resulting from a change in ambient temperature would be erroneously determined as resulting from the deterioration of the lubricant can be avoided.

In the lubricant deterioration detecting device according to the present invention, a light amount adjusting unit may be provided for adjusting an amount of light of the light source so that an output of one of the two light detecting components, which is closest the light source, attains a predetermined constant value.

With the lubricant deterioration detecting device of the construction described above, even though the amount of light received is likely to overflow or underflow as a result of a considerable change in thickness of the lubricant 6 and/or in light transmittance, the light amount adjusting unit automatically adjusts the amount of light of the light source so that the output of the light detecting component can attain a predetermined constant value and, accordingly, a stabilized detection can be accomplished. Accordingly, when the difference between the respective outputs of the two light detecting components is used, estimation of the status of deterioration of the lubricant, for example, estimation of the amount of the alien substance, generated as a result of, for example, frictional wear, which is admixed can be accomplished.

Since the distance between the light source and the light detecting components need not be fixed, the degree of freedom of arrangement comes to be high and construction is possible to accommodate to the limited space limited space available for installation. Also, because of the construction in which the signal strengths of the two light detecting components are compared to achieve the detection, a stable detection can be accomplished without adversely affected by common mode noises such as variation in electric power supply. Even though the two light detecting components are arranged within the lubricant, changes in characteristic resulting from change in temperature between the two light detecting components can be counterbalanced and, hence, an accurate detection can be accomplished.

In the lubricant deterioration detecting device according to the present invention, a light amount adjusting unit may be provided for adjusting an amount of light of the light source so that an output of one of the two light detecting components, which is remotest from the light source, attains a predetermined constant value.

Even with the lubricant deterioration detecting device of the construction described above, effects similar to those afforded by the lubricant deterioration detecting device according to the above described invention can be obtained.

In the lubricant deterioration detecting device of the present invention, an amplifying unit for amplifying an output of each of the light detecting components and a unit for adjusting a gain of the amplifying unit may be provided, in which case the determining unit compares the outputs amplified by the amplifying unit to detect the status of deterioration of the lubricant and wherein the gain adjusting unit adjusts a gain of the amplifying unit to allow the output of each of the light detecting components, which has been amplified by the amplifying unit, to attain a value within a predetermined range.

According to the lubricant deterioration detecting device of the construction described above, even though the outputs of the light detecting components amplified by the amplifying unit are likely to overflow or underflow as a result of a considerable change in thickness of the lubricant and/or in light transmittance, the gain adjusting unit adjusts the gain of the amplifying unit and, accordingly, a stable measurement can be accomplished. Accordingly, when the difference between the respective outputs of the two light detecting components is used, estimation of the status of deterioration of the lubricant, for example, estimation of the amount of the alien substance, generated as a result of, for example, frictional wear, which is admixed can be accomplished.

Since the distance between the light source and the light detecting components need not be fixed, the degree of freedom of arrangement comes to be high and construction is possible to accommodate to the limited space available for installation. Also, because of the construction in which the signal strengths of the two light detecting components are compared to achieve the detection, a stable detection can be accomplished without adversely affected by common mode noises such as variation in electric power supply. Even though the two light detecting components are arranged within the lubricant, changes in characteristic resulting from change in temperature between the two light detecting components can be counterbalanced and, hence, an accurate detection can be accomplished.

In the lubricant deterioration detecting device of the present invention, two light detecting components are provided therein and each of the light detecting components may include a detector and a optical fiber bundle having one end in the form of a base end connected with the detector and the other end in the form of a free end forming a light detecting face.

According to this construction, the amount of light attenuated after having passed across the thickness of the sample, which corresponds to the displacement in position of the free ends of the two bundles of optical fibers, can be detected by comparison of the signal outputs from the two detectors. For this reason, without being adversely affected by the thickness of the sample itself, the amount of the sample, the intensity of the light source and the distance from the light source to the light detectors, the light transmittance of the sample can be stably and accurately detected. As a result thereof, even when the transmittance detecting device is incorporated in, for example, the bearing assembly or the like, the degree of freedom of arrangement comes to be high and construction is possible to accommodate to the limited available space for installation. Also, considering that the status of deterioration of the lubricant 6 is detected by comparing the respective signal outputs of the light detectors, a stable detection can be accomplished without being adversely affected by common mode noises such as a power source variation. In addition, since the optical fibers are employed and since a sufficient light receiving surface area can be secured on the light receiving side, not only can the intensity of received light be obtained with the light detectors, but also any variation in thickness of the sample depending on the position can be cancelled and, hence, even in this respect, the light transmittance can be stably measured.

In the lubricant deterioration detecting device including the optical fiber bundles described above, a temperature sensor may be positioned proximate to the free ends of the optical fiber bundles, in which case, the use may be made of a correcting unit for correcting an output of the determining unit based on a detected value of the temperature sensor. In the case of this construction, the possibility that a change in detected signal resulting from a change in ambient temperature would be erroneously determined as resulting from the deterioration of the lubricant can be avoided.

In the lubricant deterioration detecting device including the optical fiber bundles as described above, each of the respective free ends of the optical fiber bundles may be arranged in line. In the case of this construction, since the light receiving unit can have a thin structure, deterioration of the lubricant distributed in a planar shape can be detected effectively.

In the lubricant deterioration detecting device including the bundles of optical fibers, the light source may be in the form of a linear-shaped light source corresponding to a line shaped arrangement of the free ends of the bundles of optical fibers. If the light source is employed in the form of a linear-shaped light source, the light receiving efficiency can be increased.

In the lubricant deterioration detecting device including the bundles of optical fiber, the optical fiber bundles have respective free end faces planarly arranged. The light source is preferably a planar light source corresponding to the planar shape in which the free ends of the bundle of optical fibers are arranged. In the case of this construction, averaging can be made even though the distribution of thickness of the lubricant varies and, therefore, a stable measurement can be accomplished without such variation adversely affecting the measured value. Also, merely positioning of the light source in face-to-face relation with the bundled optical fiber array having the lubricant 6 deposited on the free end face thereof makes it possible to accomplish the stabilized measurement.

A detecting device incorporated bearing assembly of the present invention is of a type in which the lubricant deterioration detecting device of any one of the constructions described above in accordance with the present invention is mounted.

According to this construction, deterioration of the lubricant filled within the bearing unit can be accurately detected in real time or regularly. As a result, prior to an actual occurrence of an abnormality in the bearing device, the necessity of replacement of the lubricant can be judged and it is possible to prevent the bearing device from being damaged as a result of the defective lubricant. Also, since the necessity of replacement of the lubricant can be determined in reference to the output of the lubricant deterioration detecting device, the amount of the lubricant which may be discarded prior to the lifetime of use can be reduced.

BRIEF DESCRIPTION OF THE DRAWINGS

In any event, the present invention will become more clearly understood from the following description of preferred embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined by the appended claims. In the accompanying drawings, like reference numerals are used to denote like parts throughout the several views, and:

FIG. 12 is a schematic structural diagram showing the lubricant deterioration detecting device according to a ninth preferred embodiment of the present invention;

DETAILED DESCRIPTION OF THE EMBODIMENTS

Figure 1A:
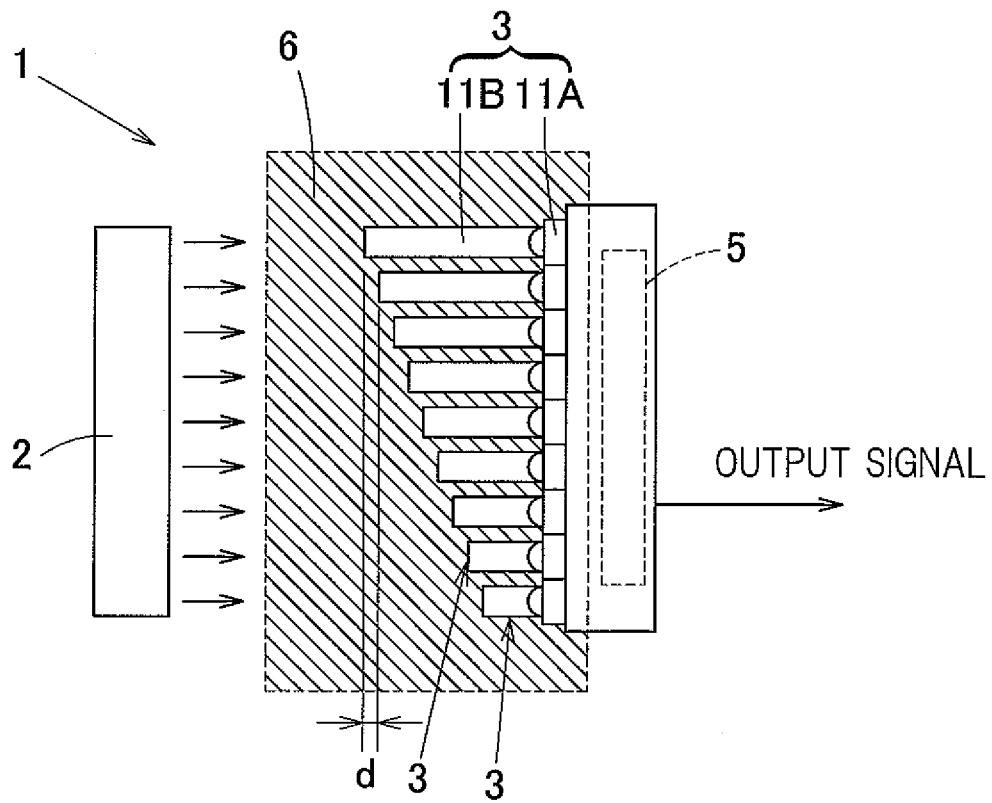
FIG. 1A is a schematic structural diagram showing a lubricant deterioration detecting device according to a first preferred embodiment of the present invention.

A first preferred embodiment of the present invention will be described with particular reference to FIGS. 1A, 1B to FIG. 3. FIG. 1A illustrates a schematic structural diagram of a lubricant deterioration detecting device according to this embodiment. This lubricant deterioration detecting device 1 includes a light source 2, a plurality of light detecting components 3 for detecting rays of light emitted from the light source 2 and subsequently transmitted through an object to be detected in the form of a lubricant 6, and a determining unit 5 for comparing respective signal strengths of outputs of the plural light detecting components 3 to detect the status of deterioration of the lubricant 6. The lubricant 6 forming the object to be detected is a lubricant filled within, for example, a bearing assembly. The plural light detecting components 3 are arranged in line and have their light detecting faces displaced sequentially a predetermined distance d in position in a direction of travel of the rays of light. Also, each of the detecting elements 3 is arranged within the lubricant 6.

In this embodiment, each of the light detecting components 3 is made up of a detector 11A and a light guide element 11B having one end in the form of a base end connected with the detector 11A and the other end in the form of a free end forming the light detecting face referred to above. The detectors 11A are formed in an array in which they are arranged in the same position relative to the direction of travel of the rays of light. In contrast thereto, the light guide elements 11B have varying lengths so that the free ends thereof occupy respective positions sequentially displaced a predetermined distance d relative to the direction of travel of the rays of light. In this way, the respective positions of the light detecting faces of the plural light detecting components are sequentially displaced the predetermined distance d relative to the direction of travel of the rays of light. For the detector 11A, a photodiode, a phototransistor, a CDS, a solar cell or a photomultiplier may be employed. Each of the light guide elements 11B is made of a transparent material such as, for example, a cylindrical synthetic resin or glass and the free end thereof, which defines the light detecting face, represents a transparent round window, and an outer peripheral surface of each of the light guide elements 11B is coated with a reflective material so that the rays of light incident on the corresponding light detecting face can travel therethrough towards the associated detector 11A.

It is to be noted that for each of the light guide elements 11B, an optical fiber may be employed. In the case that the optical fibers are employed, a detecting site, where the plural light detecting components 3 are arranged, can be thinned and, therefore, ingress of the lubricant 6 into the detecting site can be facilitated to accomplish a stabilized detection.

Also, in correspondence with the light detecting components 3 arranged in line, the light source 2 is preferably in the form of a linear-shaped light source. Where the light source 2 is in the form of the linear-shaped light source in correspondence with the line arrangement of the light detecting components 3, the intensity of light incident on the detecting site becomes uniform regardless of the position and, therefore, a stable detection can be accomplished. For the light source 2, an LED, an incandescent bulb, a semiconductor laser diode, an EL, an organic EL or a fluorescent tube may be employed.

Figure 1B:
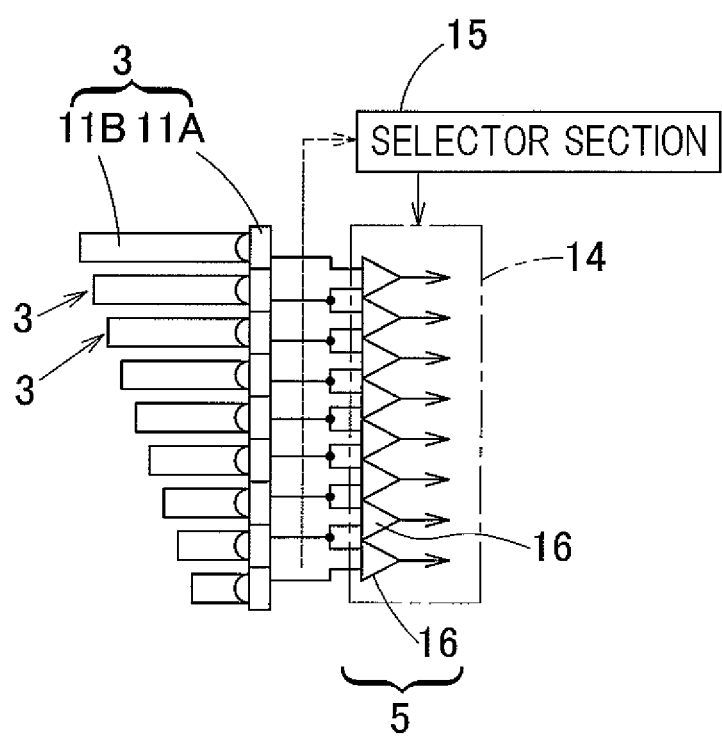
FIG. 1B is a block diagram showing a determining unit employed in the lubricant deterioration detecting device according to the first embodiment.

The determining unit 5 includes a determining section 14 and a selecting section 15 as shown in FIG. 1B. The determining section 14 is a circuit made up of, for example, a plurality of differential amplifiers 16 each operable to compare the respective signal strengths of outputs from a set of the neighboring light detecting components 3 that are displaced a distance d from each other. The selecting section 15 is a circuit operable to exclude, based on the intensity of light, some of the light detecting components 3, which generate a saturated output and/or which generate no output, and to select a result of comparison made by the determining section 14 associated with each of the sets of the neighboring light detecting components 3 that have generated a proper output.

It occurs that depending on the intensity of light emitted from the light source 2, some of the light detecting components 3 may generate a saturated output or no output. Even in such case, the comparison output from the light detecting components 3 that have generated a proper output can be selected by the selecting section 15 and, therefore, the status of deterioration of the lubricant 6 can be detected assuredly.

It is to be noted that although in FIG. 1B, the determining section 14 of the determining unit 5 has been shown and described as made up of the differential amplifiers 16 each operable to determine the difference in signal strength of the outputs of the neighboring light detecting components 3, the present invention is not always limited to the use of the differential amplifiers for the determining section 14 and any circuit configuration capable of determining the ratio of the signal strengths of the respective outputs of the neighboring light detecting components 3 may be employed.

Figure 2:
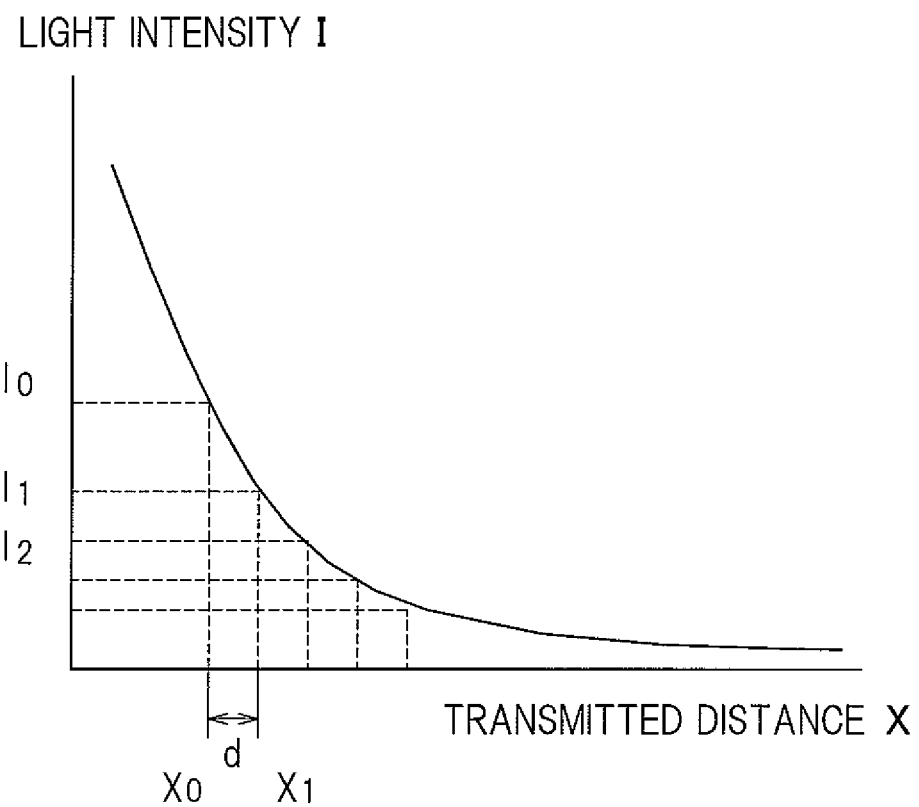
FIG. 2 is a chart showing the relation between the light transmitting distance, over which rays of light are transmitted through a lubricant, and the intensity of the transmitted light.

In the lubricant deterioration detecting device 1 of the construction described hereinabove, the intensity of light transmitted through the lubricant 6 attenuates considerably depending on the distance over which the rays of light travel. The relation between the intensity of the transmitted light and the light transmitting distance is shown in the chart of FIG. 2. This relation is expressed by the following equation (1), where the intensity of the transmitted light (the amount of the transmitted light) is expressed by I, the light transmitting distance is expressed by x and the intensity of light incident on the lubricant 6 is expressed by Iin, and α represents a constant.

$$I = I_{in} \exp(-\alpha x) \tag{1}$$

Hence, the respective signal strengths I0 and I1 of the outputs of the neighboring light detecting components 3 having light detecting faces which are held at respective locations spaced distances x0 and x1, is expressed by the following equations (2) and (3):

$$I0 = I_{in} \exp(-\alpha x0) \tag{2}$$

$$I1 = I_{in} \exp(-\alpha x1) \tag{3}$$

Where the determining unit 5 is of a type capable of determining the ratio of the respective signal strengths of the outputs of the neighboring light detecting components 3 that are displaced a distance d from each other, a detected output of the determining unit 5 is expressed by the following equation (4):

$$(I1/I0) = \exp(-\alpha(x1-x0)) = \exp(-\alpha d) \tag{4}$$

In other words, the detected output of the determining unit 5 is a value dependent on the distance d of the light detecting faces of the neighboring light detecting components 3 regardless of the thickness of the lubricant 6 itself. Since this relation establishes among the light detecting components 3 that are arrayed, the detected output of the determining unit 5 may be secured using outputs of any of the light detecting components 3.

Also, the constant α in the equation (4) above varies depending on the status of the lubricant 6. By way of example, where the lubricant 6 is of a kind filled in the bearing assembly, foreign matter such as, for example, powdery wear debris are admixed into the lubricant 6 as the bearing assembly is used in practice, and the constant α increases with an increase of the amount of the alien substance admixed. Accordingly, in the case where the determining unit 5 determines the ratio of the signal strengths of the neighboring light detecting components 3 that are displaced the distance d from each other as hereinabove described, the light transmittance of light having traveled along an optical path of the distance d in the lubricant 6 is detected and, hence, it is possible to estimate from the value of the detected output the amount of the alien substance admixed into the lubricant 6. Also, since an increase of the amount of the alien substance admixed means a progress of deterioration taking place in the lubricant 6, the determining unit 5 can detect the status of deterioration of the lubricant 6 from the amount of the alien substance estimated.

It is to be noted that the determining unit 5 referred to above may be of a type capable of determining the difference between the signal strengths of the neighboring detecting elements 3 that are displaced the distance d from each other. Since even in such case the determining unit 5 determines the light transmittance of the light transmitted the distance d in the lubricant 6, the amount of the alien substance admixed into the lubricant 6 can be estimated from the detected output thereof and, in turn, the status of deterioration of the lubricant 6 can be detected from the estimated amount of the alien substance admixed.

As hereinabove described, this lubricant deterioration detecting device 1 is so designed and so configured that while the plural light detecting components 3 are arranged with their light detecting faces held displaced the distance d from each other relative to the direction of travel of rays of light, the signal strengths of the outputs of the neighboring light detecting components 3 can be compared by the determining unit 5 to detect the status of deterioration of the lubricant 6. Accordingly, the status of deterioration of the lubricant 6 can be detected without being adversely affected by the thickness of the lubricant 6 itself, the intensity of the light source 2, and/or the distance from the light source 2 to the light detecting components 3.

Also, even in the case where, in view of the plural light detecting components 3 arranged, some of the light detecting components 3 generate a saturated output or no output depending on the intensity of light, the selecting section 15 of the determining unit 5 can select, out of a plurality of detection results generated by the determining section 14 of the determining unit 5, respective comparison outputs of each of the sets of the neighboring light detecting components 3 that provide a proper output to enable a assured detection of the status of deterioration of the lubricant 5 from a broad range of locations.

As a result, even when the lubricant deterioration detecting device 1 is incorporated in, for example, the bearing assembly or the like, degree of freedom of arrangement comes to be high and construction is possible to accommodate to the limited available space for installation. Also, considering that the status of deterioration of the lubricant 6 is detected by comparing the respective signal strengths of the outputs of the plural light detecting components 3, a stable detection can be accomplished without being adversely affected by common mode noises such as a power source variation. In addition, arrangement of the light detecting components 3 within the lubricant 6 is effective in that influences brought about by a temperature dependent change in characteristic can be counterbalanced among the neighboring light detecting components 3 and, accordingly, a highly accurate detection can be accomplished.

It is to be noted that in the construction described above, arrangement may be made that the result of detection can be made based on a change in temperature by disposing a temperature sensor in proximity of the light detecting components 3 for monitoring the temperatures of the lubricant 6 and the light detecting components 3. More specifically, for example, a circuit may be employed for correcting the detection signal generated at the temperature measured at the time of actual use, if a change in detection signal with change in temperature is beforehand measured. In such case, by sensing the temperature of the lubricant 6, it is possible to avoid the possibility that a change in detection signal with change in ambient temperature would be erroneously determined as resulting from deterioration of the lubricant 6. In this way, an accurate detection can be accomplished.

Also, in the construction described above, the determining unit 5 may include a comparing circuit for comparing a detection signal, which is obtained by comparing the respective signal strengths of the outputs from the neighboring light detecting components 3 with each other, with a predetermined reference value. In such case, the status of deterioration of the lubricant 6 can be easily determined as exceeding a predetermined level and, accordingly, it can be used as an indication of the time of replacement.

Figure 3:
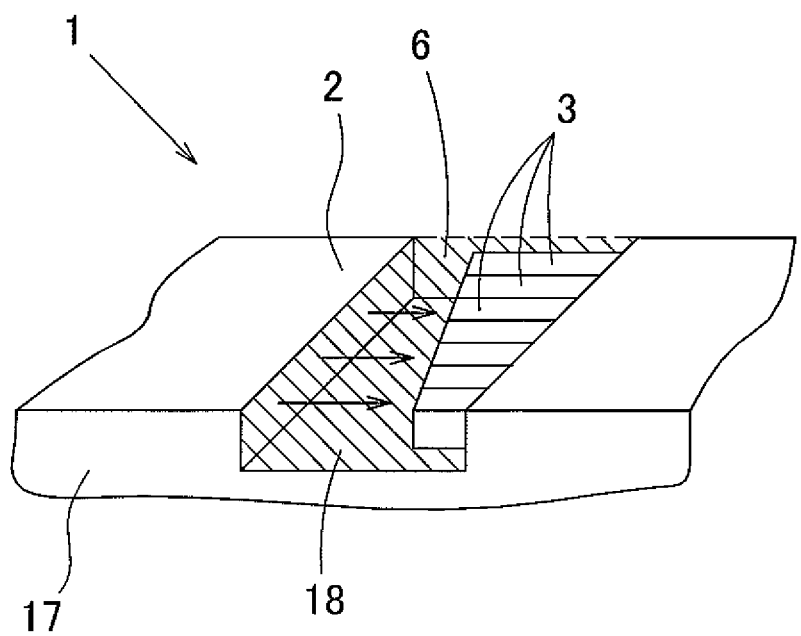
FIG. 3 is a perspective view showing a specific constructional example of the lubricant deterioration detecting device according to the first embodiment.

FIG. 3 illustrates a specific example of the lubricant deterioration detecting device 1 shown in FIG. 1A. In this example, in a planar housing 17 having a groove 18, the plural light detecting components 3 are arranged planarly along one side wall of the groove 18 and the light source 2 is arranged along the opposite side wall of the groove 18 so that the lubricant 6 flowing into the groove 18 can be detected.

Where the lubricant deterioration detecting device 1 is so constructed as hereinabove described, the status of deterioration of the lubricant 6 entering in the groove 18 and distributed on the flat can be detected.

Figure 4:
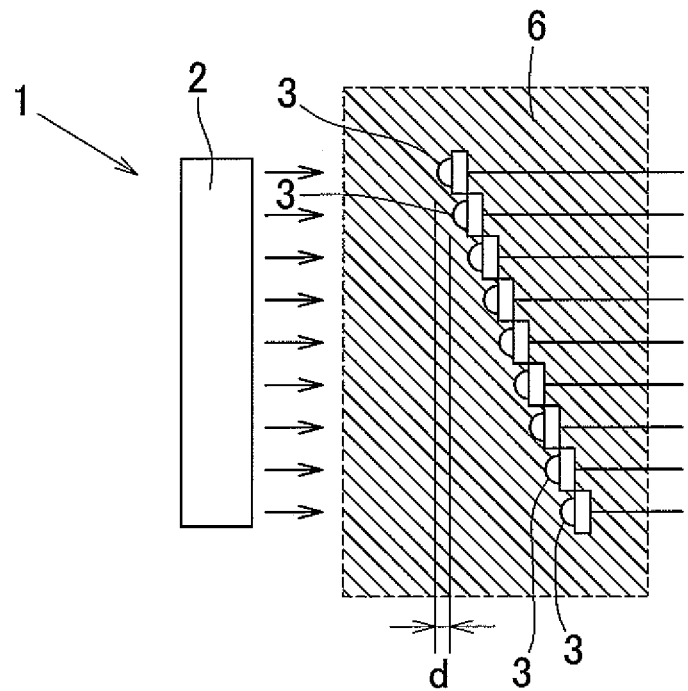
FIG. 4 is a schematic structural diagram showing a portion of the lubricant deterioration detecting device according to another preferred embodiment of the present invention.

It is to be noted that although in the embodiment shown in FIGS. 1A, 1B to 3, each of the light detecting components 3 has been shown and described as made up of the detector 11A and the light guide element 11B, but as shown in FIG. 4, the light detecting components 3 may be comprised of only the associated detectors, with the corresponding light guide element 11B dispensed of, and the detectors may be so arranged to have their light detecting faces held displaced a predetermined distance d sequentially from each other.

Figure 5:
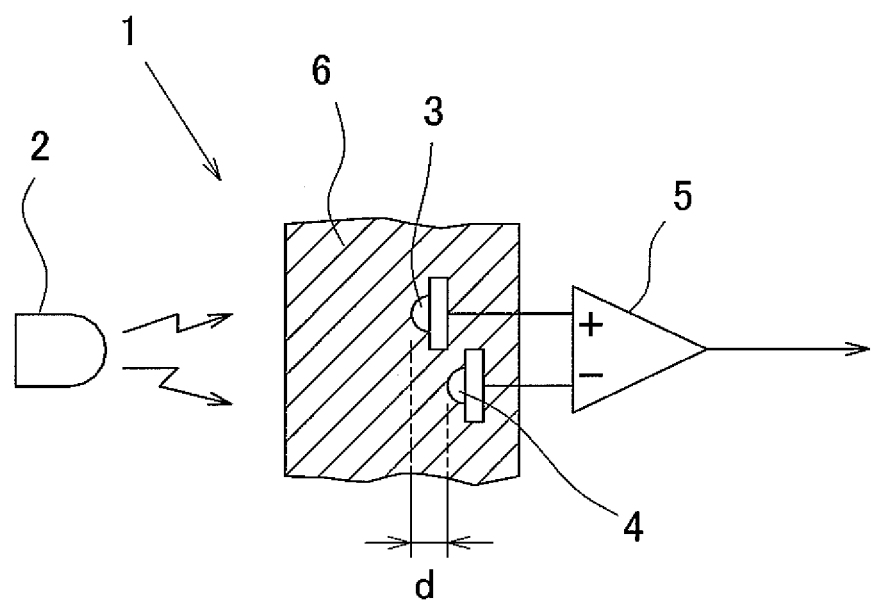
FIG. 5 is a schematic structural diagram showing the lubricant deterioration detecting device according to a second preferred embodiment of the present invention.

A second preferred embodiment of the present invention will be described with particular reference to FIG. 5. FIG. 5 illustrates a schematic structural diagram showing the lubricant deterioration detecting device according to this embodiment. This lubricant deterioration detecting device 1 includes a light source 2, two light detecting components 3 and 4 for detecting rays of light emitted from the light source 2 and subsequently transmitted through an object to be detected in the form of a lubricant 6, and a determining unit 5 for comparing respective signal strengths of outputs of the light detecting components 3 and 4 to detect the status of deterioration of the lubricant 6. The lubricant 6 forming the object to be detected is a lubricant filled within, for example, a bearing assembly. The light detecting components 3 and 4, which have their light detecting faces displaced a predetermined distance d in position in a direction of travel of the rays of light, are coupled with each other to form an integrated component part. Also, the two detecting elements 3 and 4 are arranged within the lubricant 6. In this way, the difference in thickness of the lubricant defined as a distance from a light incident surface of the lubricant 6 to the light detecting face of each of the light detecting components 3 and 4 is a value expressed by d.

For the light source 2, an LED, an incandescent bulb, a semiconductor laser diode, an EL, an organic EL or a fluorescent tube may be employed. Also, for each of the light detecting components 3 and 4, a photodiode, a phototransistor, a CDS, a solar cell or a photomultiplier may be employed. In FIG. 5, the determining unit 5 is employed in the form of a differential amplifying circuit capable of determining the difference between the respective signal strengths of the outputs of the two light detecting components 3 and 4, but the present invention may not always limited thereto and any circuit configuration capable of determining the ratio of the signal strengths of the respective outputs of the two light detecting components 3 and 4 may be employed.

Also, the constant α in the equation (4) described previously varies depending on the status of the lubricant 6. By way of example, where the lubricant 6 is of a kind filled in the bearing assembly, foreign matter such as, for example, powdery wear debris are admixed into the lubricant 6 as the bearing assembly is used in practice and, accordingly, the constant α increases with an increase of the amount of the alien substance admixed. Therefore, in the case where the determining unit 5 determines the ratio of the signal strengths of the light detecting components 3 and 4 as hereinabove described, the light transmittance of light having traveled the distance d within the lubricant 6 is detected and, hence, it is possible to estimate from the value of the detected output the amount of the alien substance admixed into the lubricant 6. Also, since an increase of the amount of the alien substance admixed means a progress of deterioration taking place in the lubricant 6, the determining unit 5 can detect the status of deterioration of the lubricant 6 from the amount of the alien substance estimated.

It is to be noted that the determining unit 5 may be of a type capable of determining the difference between the respective signal strengths of the two light detecting components 3 and 4. Even in this case, the determining unit 5 detects the light transmittance of rays of light transmitted the distance d within the lubricant 6 and, accordingly, the amount of the alien substance admixed into the lubricant 6 can be estimated from the detected output thereof and the status of deterioration of the lubricant 6 can accordingly detected from the amount of the alien substances so estimated.

As hereinabove described, this lubricant deterioration detecting device 1 is so designed that the two light detecting components 3 and 4 are arranged with their light detecting faces displaced from each other the distance d relative to the direction of travel of the rays of light so that the respective signal strengths of the outputs of the two light detecting components 3 and 4 can be compared by the determining unit 5 to detect the status of deterioration of the lubricant 6. Accordingly, the status of deterioration of the lubricant 6 can be detected without being adversely affected by the thickness of the lubricant 6 itself, the intensity of the light source 2 and/or the distance from the light source 2 to the light detecting components 3 and 4.

As a result, even when the lubricant deterioration detecting device 1 is incorporated in, for example, the bearing assembly or the like, the degree of freedom of arrangement comes to be high and construction is possible to accommodate to the limited available space for installation. Also, considering that the status of deterioration of the lubricant 6 is detected by comparing the respective signal strengths of the outputs of the light detecting components 3 and 4, a stable detection can be accomplished without being adversely affected by common mode noises such as a power source variation. In addition, arrangement of the light detecting components 3 and 4 within the lubricant 6 is effective in that influences brought about by a temperature dependent change in characteristic of those two light detecting components 3 and 4 can be counterbalanced and, accordingly, a highly accurate detection can be accomplished.

It is to be noted that in the construction described above, arrangement may be made that the result of detection can be made based on a change in temperature by disposing a temperature sensor in proximity of the two light detecting components 3 and 4 for monitoring the temperatures of the lubricant 6 and the light detecting components 3 and 4. More specifically, for example, a circuit may be employed for correcting the detection signal generated at the temperature measured at the time of actual use, if a change in detection signal with change in temperature is beforehand measured. In such case, by sensing the temperature of the lubricant 6, it is possible to avoid the possibility that a change in detection signal with change in ambient temperature would be erroneously determined as resulting from deterioration of the lubricant 6. In this way, an accurate detection can be accomplished.

Also, in the construction described above, the determining unit 5 may include a comparing circuit for comparing a detection signal, which is obtained by comparing the respective signal strengths of the outputs from the two light detecting components 3 and 4 with each other, with a predetermined reference value. In such case, the status of deterioration of the lubricant 6 can be easily determined as exceeding a predetermined level and, accordingly, it can be used as an indication of the time of replacement.

Figure 6:
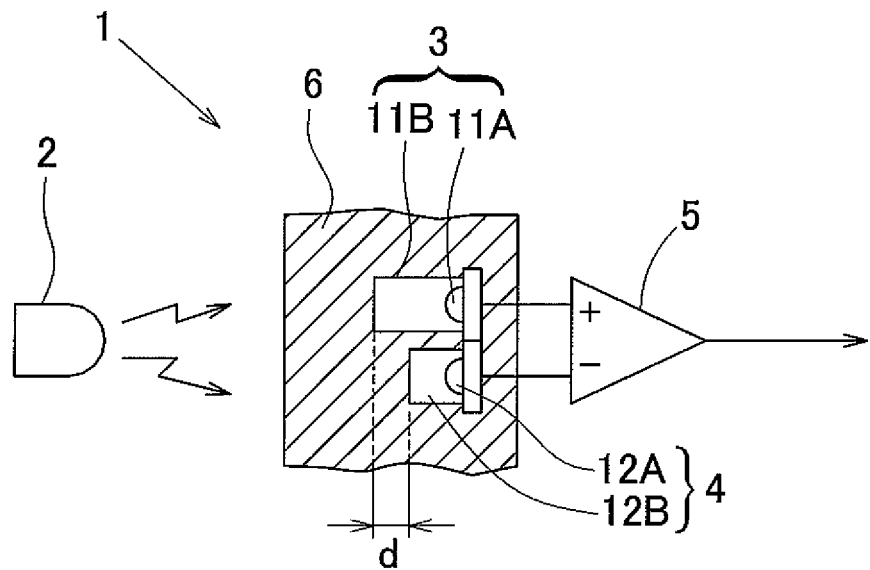
FIG. 6 is a schematic structural diagram showing the lubricant deterioration detecting device according to a third preferred embodiment of the present invention.

FIG. 6 illustrates a schematic structural diagram showing the lubricant deterioration detecting device according to a third preferred embodiment of the present invention. This lubricant deterioration detecting device 1 is similar to that according to the second embodiment shown in and described with reference to FIG. 5, but differs therefrom in that the two light detecting components 3 and 4 are respectively made up of a detector 11A and 12A and a light guide element 11B and 12B. More specifically, one of the light detecting components 3 is made up of the detector 11A and the light guide element 11B having a base end connected with the detector 11A and a free end defining a light detecting face, while the other of the light detecting component 4 is made up of the detector 12A and the light guide element 12B having a base end connected with the detector 12A and a free end defining a light detecting face. For each of the detectors 11A and 12A, a photodiode, a phototransistor, a CDS, a solar cell or a photomultiplier may be employed. In this case, the two detectors 11A and 12A are juxtaposed at the same position relative to the direction of travel of the rays of light. In contrast thereto, the two light guide elements 11B and 12B have varying lengths so that their free ends are held displaced the predetermined distance d from each other relative to the direction of travel of the rays of light. Accordingly, the respective positions of the light detecting faces of those two light detecting components 3 and 4 are displaced the predetermined distance d from each other relative to the direction of travel of the rays of light. Each of the light guide elements 11B and 12B is made of a transparent material such as, for example, a cylindrical synthetic resin or glass and the free end thereof, which defines the light detecting face, represents a transparent round window, and an outer peripheral surface of each of the light guide elements 11B and 12B is coated with a reflective material. It is to be noted that each of the light guide elements 11B and 12B may not be always limited to that having a cylindrical shape, but may have a rectangular sectioned tubular shape. Other structural features than those described above are similar to those employed in the second embodiment.

Even in the case of the lubricant deterioration detecting device 1, since the two light detecting components 3 and 4 are so arranged as to have their light detecting faces held displaced the distance d from each other relative to the direction of travel of the rays of light, the status of deterioration of the lubricant 6 can be detected without being adversely affected by thickness of the lubricant 6 itself, the intensity of the light source 2 and/or the distance from the light source 2 to the light detecting components 3 and 4.

Figure 7:
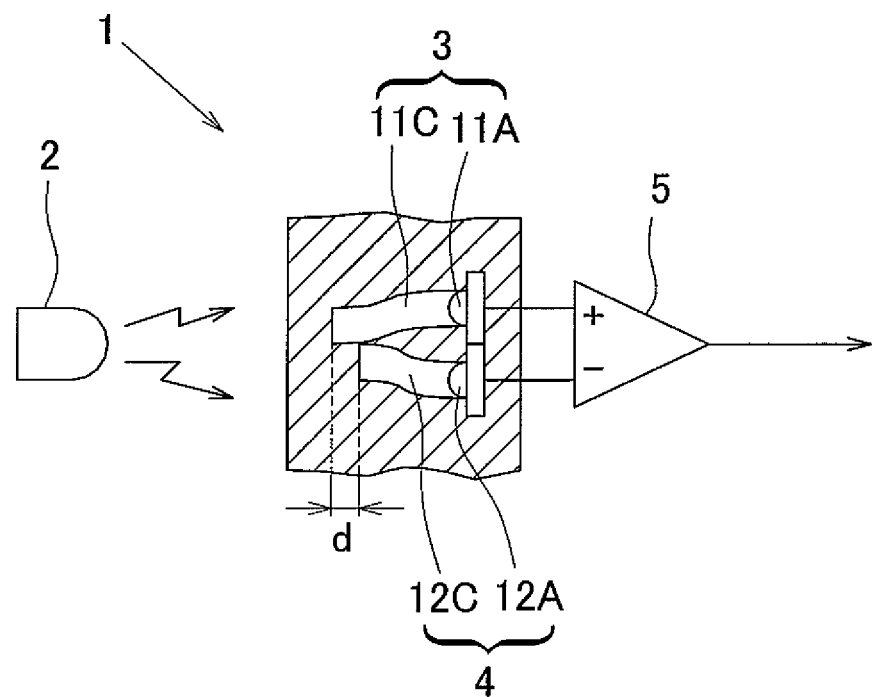
FIG. 7 is a schematic structural diagram showing the lubricant deterioration detecting device according to a fourth preferred embodiment of the present invention.

FIG. 7 illustrates a schematic structural diagram showing a fourth preferred embodiment of the present invention. The lubricant deterioration detecting device 1 according to this embodiment is similar to that according to the second embodiment shown in and described with reference to FIG. 5, but differs therefrom in that the two light detecting components 3 and 4 are respectively made up of a detector 11A and 12A and an optical fiber 11C and 12C. More specifically, the light detecting component 3 is made up of the detector 11A and the optical fiber 11C having a base end connected with the detector 11A and a free end defining the light detecting face, while the light detecting components 4 is made up of the detector 12A and the optical fiber 12C having a base end connected with the detector 12A and a free end defining the light detecting face. For each of the detectors 11A and 12A, a photodiode, a phototransistor, a CDS, a solar cell or a photomultiplier may be employed. In this case, the two detectors 11A and 12A are juxtaposed at the same position relative to the direction of travel of the rays of light and the two optical fibers 11C and 12C have varying lengths so that their free ends held displaced a predetermined distance d relative to the direction of travel of the rays of light. Accordingly, the respective positions of the light detecting faces of those two light detecting components 3 and 4 are displaced the predetermined distance d from each other relative to the direction of travel of the rays of light. Other structural features than those described above are similar to those employed in the second embodiment.

Even in the case of the lubricant deterioration detecting device 1, since the two light detecting components 3 and 4 are so arranged as to have their light detecting faces held displaced the distance d from each other relative to the direction of travel of the rays of light, the status of deterioration of the lubricant 6 can be detected without being adversely affected by thickness of the lubricant 6 itself, the intensity of the light source 2 and/or the distance from the light source 2 to the light detecting components 3 and 4.

Figure 8:
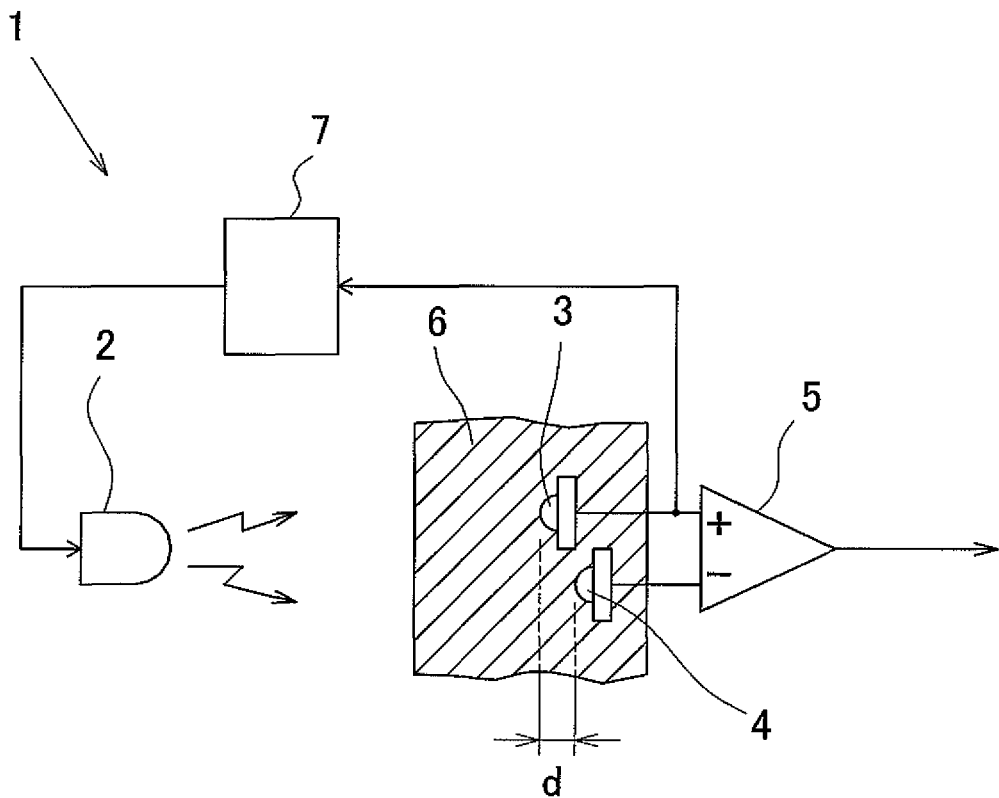
FIG. 8 is a schematic structural diagram showing the lubricant deterioration detecting device according to a fifth preferred embodiment of the present invention.

A fifth preferred embodiment of the present invention will now be described with particular reference to FIG. 8. FIG. 8 illustrates a schematic structural diagram showing the lubricant deterioration detecting device according to this embodiment. This lubricant deterioration detecting device 1 includes a light source 2, two light detecting components 3 and 4 for detecting rays of light emitted from the light source 2 and subsequently transmitted through an object to be detected in the form of a lubricant 6, a determining unit 5 for comparing respective signal strengths of outputs of the light detecting components 3 and 4 to detect the status of deterioration of the lubricant 6, and a light amount adjusting unit 7 for adjusting the amount of light emitted by the light source 2. The lubricant 6 forming an object to be detected is a lubricant filled within, for example, a bearing assembly. The light detecting components 3 and 4, which have their light detecting faces displaced a predetermined distance d in position in a direction of travel of the rays of light, are coupled with each other to form an integrated component part. Also, the two detecting elements 3 and 4 are arranged within the lubricant 6. Hence, the difference in thickness of the lubricant defined as a distance from a light incident surface of the lubricant 6 to the light detecting face of each of the light detecting components 3 and 4 is a value expressed by d.

For the light source 2, an LED, an incandescent bulb, a semiconductor laser diode, an EL, an organic EL or a fluorescent tube may be employed. Also, for each of the light detecting components 3 and 4, a photodiode, a phototransistor, a CDS, a solar cell or a photomultiplier may be employed. In FIG. 8, the determining unit 5 is employed in the form of a differential amplifying circuit capable of determining the difference between the respective signal strengths of the outputs of the two light detecting components 3 and 5, but the present invention may not always limited thereto and any circuit configuration capable of determining the ratio of the signal strengths of the respective outputs of the two light detecting components 3 and 4 may be employed.

The light amount adjusting unit 7 is operable to adjust the amount of light emitted from the light source 2 so that an output of one of the two light detecting components 3 and 4 that is closest to the light source 2, that is, an output of the light detecting component 3 (or the amount of light incident on the light detecting component 3) can represent a predetermined proper constant value (or a value within a constant range) by judging based on an output of the light detecting component 3. In this case, the proper constant value (or the value within the constant range) represented by the output of the light detecting component 3 means a value representing proper output of the light detecting component 3 corresponding to the amount of light received thereby without being saturated. It is to be noted that the amount of light received by the light detecting component 4 remote from the light source 2 does not exceed the amount of light received by the light detected element 3 closest to the light source 2 and, therefore, by setting the output of the light detecting component 3 to a value as large as possible unless saturated, a highly precise detecting system can be obtained.

The light amount adjusting unit may be composed of either an electronic circuit or that having a calculator or a built-in computer. Also, adjustment of the amount of light of the light source 2 accomplished by the light amount adjusting unit 7 may be performed either automatically continuously or intermittently only at the time of detection for the status of deterioration of the lubricant 6. In addition, where heat evolution of the light source 2 is requested to be suppressed or the maximum amount of light is desired to be increased, it is preferred that the light source 2 may be lit only at the time of detection of the status of deterioration of the lubricant 6, instead of being lit continuously.

Also, the constant α in the equation (4) above varies depending on the status of the lubricant 6. By way of example, where the lubricant 6 is of a kind filled in the bearing assembly, foreign matter such as, for example, powdery wear debris are admixed into the lubricant 6 as the bearing assembly is used in practice, the constant α increases with an increase of the amount of the alien substance admixed. Accordingly, in the case where the determining unit 5 determines the ratio of the signal strengths of the two light detecting components 3 and 4 as hereinabove described, the light transmittance of light having traveled along an optical path of the distance d in the lubricant 6 is detected and, hence, it is possible to estimate from the value of the detected output the amount of the alien substance admixed into the lubricant 6. Also, since an increase of the amount of the alien substance admixed means a progress of deterioration taking place in the lubricant 6, the determining unit 5 can detect the status of deterioration of the lubricant 6 from the amount of the alien substance estimated.

It is to be noted that the determining unit 5 referred to above may be of a type capable of determining the difference between the signal strengths of the two detecting elements 3 and 4 referred to above. Since even in such case the determining unit 5 determines the light transmittance of the light transmitted the distance d in the lubricant 6, the amount of the alien substance admixed into the lubricant 6 can be estimated from the detected output thereof and, in turn, the status of deterioration of the lubricant 6 can be detected from the estimated amount of the alien substance admixed.

Also, even though the amount of light received is likely to overflow or underflow as a result of a considerable change in thickness of the lubricant 6 and/or in light transmittance, the light amount adjusting unit 7 automatically adjusts the amount of light of the light source 2 (to allow the output of the light detecting component 4 to attain a proper value) so that the output of the light detecting component 3 can attain a predetermined proper constant value (or a value within the constant range) and, accordingly, a stabilized detection can be accomplished.

As hereinabove described, this lubricant deterioration detecting device 1 is so designed and so configured that while the two light detecting components 3 and 4 are arranged with their light detecting faces held displaced the distance d from each other relative to the direction of travel of rays of light, the signal strengths of the outputs of the two light detecting components 3 and 4 can be compared by the determining unit 5 to detect the status of deterioration of the lubricant 6, and the amount of light of the light source 2 is automatically adjusted by the light amount adjusting unit 7. Accordingly the status of deterioration of the lubricant 6 can be detected without being adversely affected by the thickness of the lubricant 6 itself, the intensity of the light source 2 and/or the distance from the light source 2 to the light detecting components 3.

As a result, even when the lubricant deterioration detecting device 1 is incorporated in, for example, the bearing assembly or the like, the degree of freedom of arrangement comes to be high and construction is possible to accommodate to the limited available space for installation. Also, considering that the status of deterioration of the lubricant 6 is detected by comparing the respective signal strengths of the outputs of the two light detecting components 3 and 4, a stable detection can be accomplished without being adversely affected by common mode noises such as a power source variation. In addition, arrangement of the two light detecting components 3 and 4 within the lubricant 6 is effective in that influences brought about by a temperature dependent change in characteristic can be counterbalanced among the two light detecting components 3 and 4 and, accordingly, a highly accurate detection can be accomplished.

It is to be noted that in the construction described above, arrangement may be made that the result of detection can be made based on a change in temperature by disposing a temperature sensor in proximity of the light detecting components 3 and 4 for monitoring the temperatures of the lubricant 6 and the light detecting components 3 and 4. More specifically, for example, a circuit may be employed for correcting the detection signal generated at the temperature measured at the time of actual use, if a change in detection signal with change in temperature is beforehand measured. In such case, by sensing the temperature of the lubricant 6, it is possible to avoid the possibility that a change in detection signal with change in ambient temperature would be erroneously determined as resulting from deterioration of the lubricant 6. In this way, an accurate detection can be accomplished.

Also, in the construction described above, the determining unit 5 may include a comparing circuit for comparing a detection signal, which is obtained by comparing the respective signal strengths of the outputs from the two light detecting components 3 and 4 with each other, with a predetermined reference value. In such case, the status of deterioration of the lubricant 6 can be easily determined as exceeding a predetermined level and, accordingly, it can be used as an indication of the time of replacement.

Figure 9:
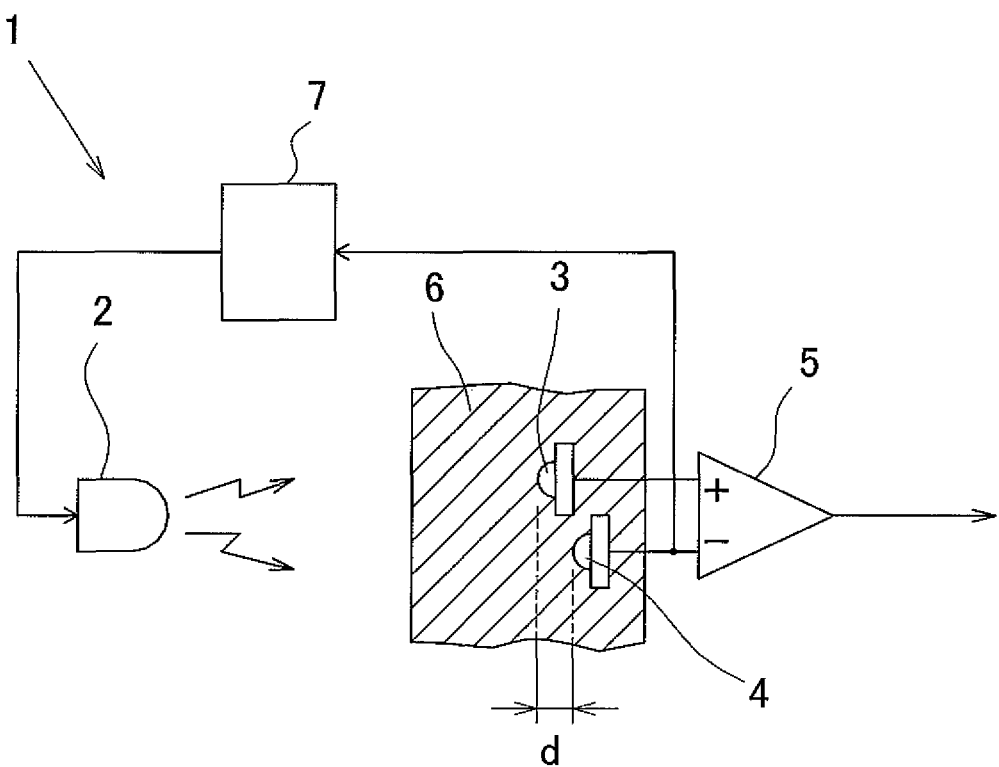
FIG. 9 is a schematic structural diagram showing the lubricant deterioration detecting device according to a sixth preferred embodiment of the present invention.

FIG. 9 illustrates a schematic structural diagram showing a sixth preferred embodiment of the present invention. The lubricant deterioration detecting device 1 according to this embodiment is similar to that according to the fifth embodiment shown in and described with particular reference to FIG. 8, but differs therefrom in that the light amount adjusting unit 7 is designed to adjust the amount of light emitted from the light source 2 so that an output of one of the two light detecting components 3 and 4, that is remotest to the light source 2, that is, an output of the light detecting component 4 (or the amount of light incident on the light detecting component 4) can represent a predetermined proper constant value (or a value within a constant range) by judging based on an output of the light detecting component 4. In this case, since there is the possibility that even though the output of the light detecting component 4 remotest to the light source 2 is a proper value, the output of the light detecting component 3 closest to the light source 2 may be saturated, it is necessary to set the predetermined proper constant value (or a value within the constant range) for the output of the light detecting component 4 to a low value so that the output of the light detecting component 3 will not be saturated. Other structural features than those described above are similar to those shown and described in connection with the fifth embodiment, and the same is true of the effects.

Figure 10:
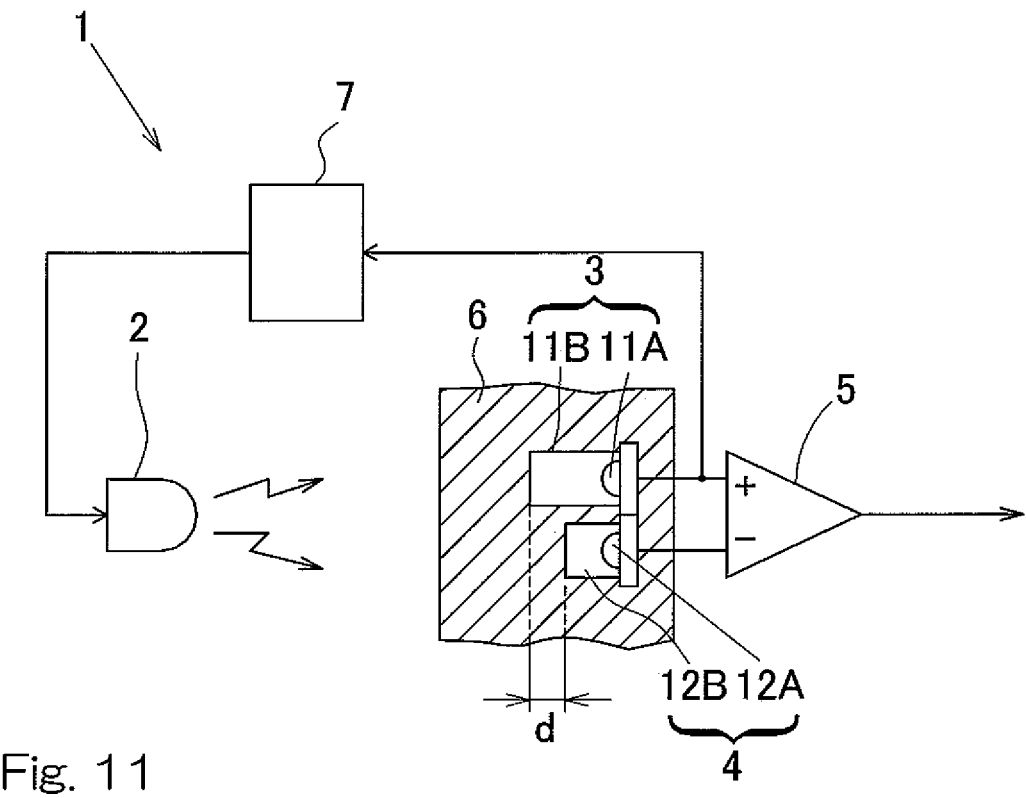
FIG. 10 is a schematic structural diagram showing the lubricant deterioration detecting device according to a seventh preferred embodiment of the present invention.

FIG. 10 illustrates a schematic structural diagram showing a seventh preferred embodiment of the present invention. The lubricant deterioration detecting device 1 according to this embodiment is similar to that according in the fifth embodiment shown in and described with reference to FIG. 8, but differs therefrom in that the two light detecting components 3 and 4 are respectively made up of detectors 11A and 12A and light guide elements 11B and 12B. In other words, the light detecting components 3 is made up of the detector 11A and the light guide element 11B having a base end connected with the detector 11A and a free end forming the light detecting face, while the light detecting component 4 is made up of the detector 12A and the light guide element 12B having a base end connected with the detector 12A and a free end defining the light detecting face. For each of the detectors 11A and 12A, a photodiode, a phototransistor, a CDS, a solar cell or a photomultiplier may be employed. In this case, the two detectors 11A and 12A are juxtaposed at the same position relative to the direction of travel of the rays of light and the two light guide elements 11B and 12B have varying lengths so that their free ends are held displaced the predetermined distance d from each other relative to the direction of travel of the rays of light. Accordingly, the respective positions of the light detecting faces of those two light detecting components 3 and 4 are displaced the predetermined distance d from each other relative to the direction of travel of the rays of light. Each of the light guide elements 11B and 12B is made of a transparent material such as, for example, a cylindrical synthetic resin or glass and the free end thereof, which defines the light detecting face, represents a transparent round window, and an outer peripheral surface of each of the light guide elements 11B and 12B is coated with a reflective material. It is to be noted that each of the light guide elements 11B and 12B may not be always limited to that having a cylindrical shape, but may have a rectangular sectioned tubular shape. Other structural features than those described above are similar those according to the fifth embodiment.

Even in the case of the lubricant deterioration detecting device 1 of the construction described above, since the two light detecting components 3 and 4 are arranged with their light detecting faces displaced from each other the distance d relative to the direction of travel of the rays of light, the status of deterioration of the lubricant 6 can be detected without being adversely affected by the thickness of the lubricant 6 itself the intensity of the light source 2 and/or the distance from the light source 2 to the light detecting components 3 and 4.

It is to be noted that in this embodiment, the light amount adjusting unit 7 may be so designed as to adjust the amount of light of the light source 2 based on the output of the light detecting component 4, that is remotest from the light source 2.

Figure 11:
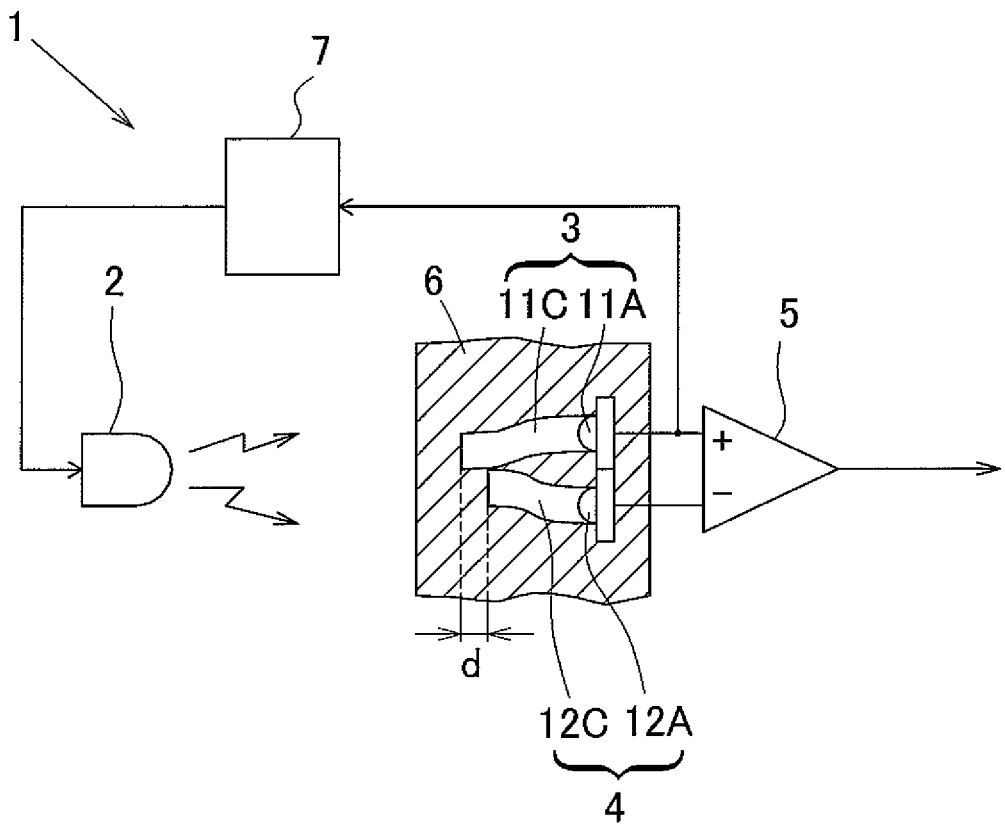
FIG. 11 is a schematic structural diagram showing the lubricant deterioration detecting device according to an eighth preferred embodiment of the present invention.

FIG. 11 illustrates a schematic structural diagram showing an eighth preferred embodiment of the present invention. The lubricant deterioration detecting device 1 according to this embodiment is similar to that according to the fifth embodiment shown in and described with reference to FIG. 8, but differs therefrom in that the two light detecting components 3 and 4 are respectively made up of a detector 11A and 12A and an optical fiber 11C and 12C. In other words, the light detecting component 3 is made up of the detector 11A and the optical fiber 11C having a base end connected with the detector 11A and a free end defining the light detecting face, while the light detecting component 4 is made up of the detector 12A and the optical fiber 12C having a base end connected with the detector 12A and a free end defining the light detecting face. For each of the detectors 11A and 12A, a photodiode, a phototransistor, a CDS, a solar cell or a photomultiplier may be employed. In this case, the two detectors 11A and 12A are juxtaposed at the same position relative to the direction of travel of the rays of light and the two optical fibers 11C and 12C have their free ends held displaced a predetermined distance d relative to the direction of travel of the rays of light, as is the case with the embodiment shown in and described with reference to FIG. 10. Even in this case, the two detectors 11A and 12A are juxtaposed at the same position relative to the direction of travel of the rays of light and the two optical fibers 11C and 12C have different lengths so that the free ends thereof can be held displaced from each other a predetermined distance d relative to the direction of travel of the rays of light. Accordingly, the respective positions of the light detecting faces of those two light detecting components 3 and 4 are displaced the predetermined distance d from each other relative to the direction of travel of the rays of light. Other structural features than those described above are similar to those employed in the fifth embodiment.

Even in the case of the lubricant deterioration detecting device 1, since the two light detecting components 3 and 4 are so arranged as to have their light detecting faces held displaced the distance d from each other relative to the direction of travel of the rays of light, the status of deterioration of the lubricant 6 can be detected without being adversely affected by thickness and/or light transmittance of the lubricant 6 itself, the intensity of the light source 2 and/or the distance from the light source to the light detecting components 3 and 4.

A ninth preferred embodiment of the present invention will now be described with particular reference to FIGS. 12 to 16. FIG. 12 illustrates a schematic structural diagram showing the lubricant deterioration detecting device according to this embodiment. This lubricant deterioration detecting device 1 includes a light source 2, two light detecting components 3 and 4 for detecting rays of light emitted from the light source 2 and subsequently transmitted through an object to be detected in the form of a lubricant 6, amplifying units 20 and 21 for amplifying respective outputs of the two light detecting components 3 and 4, a determining unit 5 for comparing respective signal strengths of the outputs amplified by those amplifying units 20 and 21 to detect the status of deterioration of the lubricant 6, and gain adjusting units 24 and 25 for adjusting respective gains of the amplifying units 20 and 21. The lubricant 6 forming an object to be detected is a lubricant filled within, for example, a bearing assembly. The light detecting components 3 and 4, which have their light detecting faces displaced a predetermined distance d in position in a direction of travel of the rays of light, are coupled with each other to form an integrated component part. Also, the two detecting elements 3 and 4 are arranged within the lubricant 6. In this way, the difference in thickness of the lubricant defined as a distance from a light incident surface of the lubricant 6 to the light detecting face of each of the light detecting components 3 and 4 is a value expressed by d.

For the light source 2, an LED, an incandescent bulb, a semiconductor laser diode, an EL, an organic EL or a fluorescent tube may be employed. Also, for each of the light detecting components 3 and 4, a photodiode, a phototransistor, a CDS, a solar cell or a photomultiplier may be employed. In FIG. 12, the determining unit 5 is employed in the form of a differential amplifying circuit capable of determining the difference between the respective signal strengths of the outputs of the light detecting components 3 and 4 amplified by the respective amplifying units 20 and 21, but the present invention may not always limited thereto and any circuit configuration capable of determining the ratio of the signal strengths of the respective outputs of the two light detecting components 3 and 4 may be employed.

Each of the gain adjusting units 24 and 25 is operable to adjust the gain of the associated amplifying units 20 and 21 so that the output of the respective light detecting component 3 and 4 can attain a value within a predetermined range.

Figure 13:
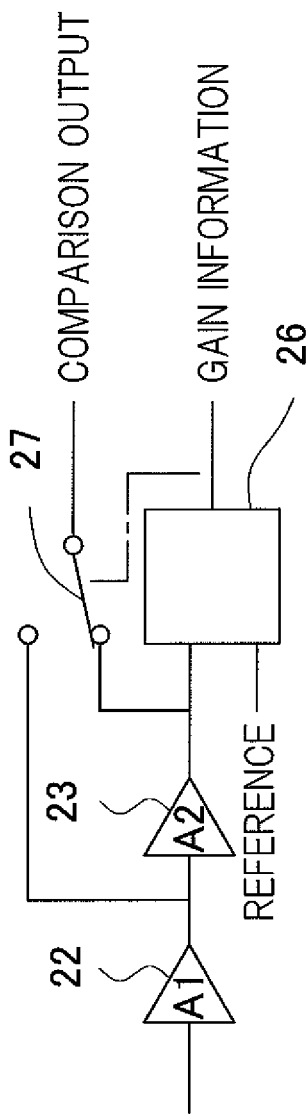
FIG. 13 is a specific structural diagram showing an amplifying unit and a gain adjusting unit both employed in the lubricant deterioration detecting device.

FIG. 13 illustrates a constructional example of the amplifying unit 20 (21) and the associated gain adjusting unit 24 (25). The amplifying unit 20 (21) includes two, amplifiers 22 and 23, connected with each other in series, having respective constant gains A1 and A2. The gain of the amplifying unit 20 (21) as a whole is obtained from A1×A2, in the case of the maximum amplification factor. The gain adjusting unit 24 (25) is made up of a comparator 26 and a switch 27. The comparator 26 is operable to compare an output from the amplifier 23 with a reference value and, in the event that the output of the amplifier 23 exceeds the reference value, it determines that that output from the amplifier 23 is in an overflowing condition and then generates a command to trigger the switch 27 so that the overall gain of the amplifying unit 20 (21) can be switched from A1×A2 to A1. While the output of the amplifying unit 20 (21) is supplied to the determining unit 5 in the subsequent stage as an output for comparison, the determining unit 5 detects the status of deterioration (the light transmittance) of the lubricant 6 with information on the gain of the comparator 26 taken into consideration.

Figure 14:
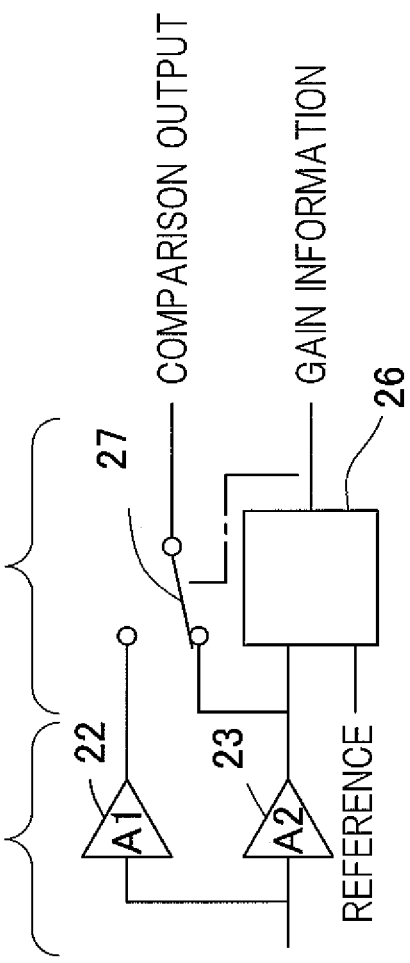
FIG. 14 is another specific structural diagram showing the amplifying unit and the gain adjusting unit both employed in the lubricant deterioration detecting device.

FIG. 14 illustrates another constructional example of the amplifying unit 20 (21) and the gain adjusting unit 24 (25). The amplifying unit 20 (21) is made up of two amplifiers 22 and 23, connected with each other in parallel, having respective constant gains A1 and A2. In this case, the gain A1 is rendered to be a low gain and the gain A2 is rendered to be a high gain. Other structural features are similar to those shown in and described with reference to FIG. 13. The operation thereof is also similar to that of the constructional example shown in and described with reference to FIG. 13 and, in the event that the output of the amplifier 23 exceeds the reference value, it determines that an output from the amplifier 23 is in an overflowing condition and then generates a command to trigger the switch 27 so that the overall gain of the amplifying unit 20 (21) can be switched from A2 over to A1. The number of the amplifiers forming the amplifying unit 20 (21) is not always limited to two such as shown, a multitude of amplifiers may be employed therefor.

Figure 15:
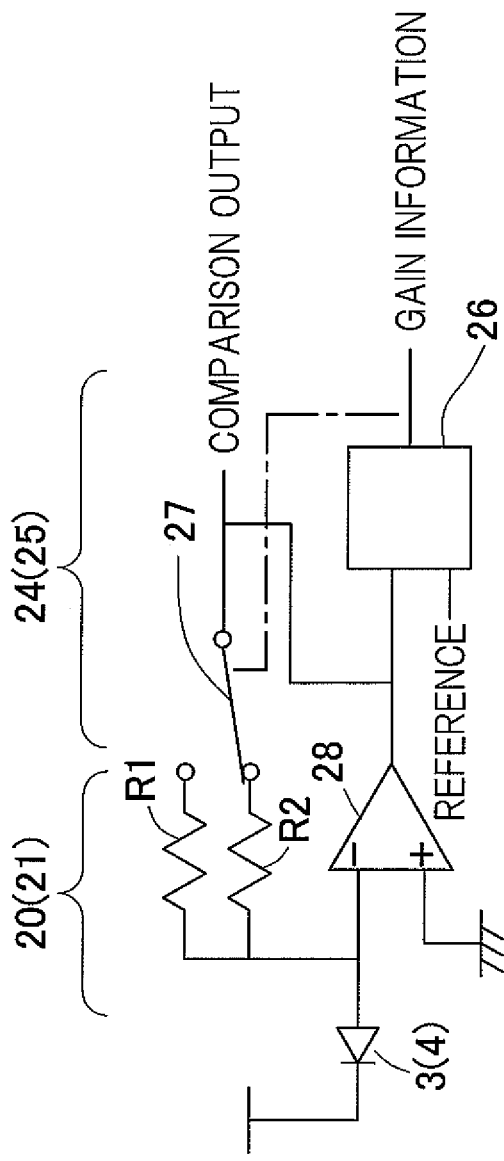
FIG. 15 is a further specific structural diagram showing the amplifying unit and the gain adjusting unit both employed in the lubricant deterioration detecting device.

FIG. 15 illustrates a further constructional example of the amplifying unit 20 (21) and the gain adjusting unit 24 (25). The amplifying unit 20 (21) is structured in the form of an inverting amplifier that is made up of an operational amplifier 28 and parallel connected current-voltage converting resistors R1 and R2 connected with each other in parallel. On an input side of the operational amplifier 28, the respective light detecting component 3 (4) in the form of photodiode is connected in series with the two resistors R1 and R2 connected with each other in parallel. The resistor R1 is set to have a low resistance and the resistor R2 is set to have a high resistance. Similarly to the constructional example shown in and described with reference to FIG. 13, the gain adjusting unit 24 (25) is made up of a comparator 26 and a switch 27. The comparator 26 is operable to compare an output from the operational amplifier 28 with a reference value and, in the event that the output of the operational amplifier 28 exceeds the reference value, it determines that an output from the amplifier 23 is in an overflowing condition and then generates a command to trigger the switch 27. By so doing, the resistor which is to be used for the current-voltage conversion can be switched from resistor R2 to resistor R1 to thereby lower the overall gain. It is to be noted that in this constructional example, arrangement may be made so that instead of the switching taking place from the resistor R2 to the resistor R1, connection is normally made with only the resistor R2, but only when the output of the operational amplifier 28 exceeds the reference value, the resistor R1 can be connected in parallel to the resistor R2.

Figure 16:
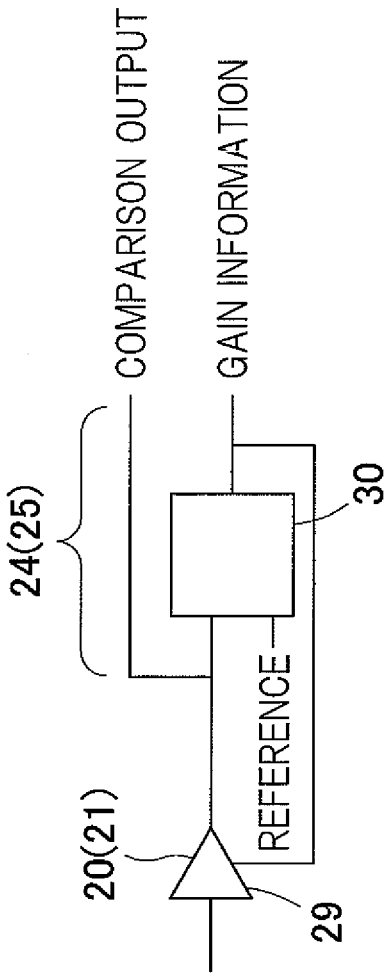
FIG. 16 is a yet further specific structural diagram showing the amplifying unit and the gain adjusting unit both employed in the lubricant deterioration detecting device.

FIG. 16 illustrates a still further constructional example of the amplifying unit 20 (21) and the gain adjusting unit 24 (25). The amplifying unit 20 (21) is employed in the form of a voltage controlled amplifier (VCA) 29 and the gain adjusting unit 24 (25) is employed in the form of a control voltage generator 30. The control voltage generator 30 compares an output of the voltage controlled amplifier 29 with a reference value in order to feedback an output voltage, which is a result of the comparison performed thereby to the voltage controlled amplifier 29, whereby the gain of the voltage controlled amplifier 29 is changed by this output voltage. In other words, when the output of the voltage controlled amplifier 29 is, for example, higher than the reference value, the output voltage of the control signal generator 30 becomes lower and the gain of the voltage controlled amplifier 29, to which this low output voltage is feedback, lowers. On the other hand, when the output of the voltage controlled amplifier 29 is lower than the reference value, the output voltage of the control voltage generator 30 becomes higher and the gain of the voltage controlled amplifier 29, to which this high output voltage is fed back, increases.

In this way, this constructional example can have a function equivalent to the switching performed by the switch 27 in any one of the constructional examples hereinabove described. In such case, a change of the gain of the voltage controlled amplifier 29 may be in a multi-step fashion or a non-step fashion.

The constant $\alpha$ in the equation (4) described previously varies depending on the status of the lubricant 6. By way of example, where the lubricant 6 is of a kind filled in the bearing assembly, foreign matter such as, for example, powdery wear debris are admixed into the lubricant 6 as the bearing assembly is used in practice and, accordingly, the constant $\alpha$ increases with an increase of the amount of the alien substance admixed. Therefore, in the case where the amplifying units 20 and 21 have the same gain and the determining unit 5 determines the ratio of the signal strengths of the respective outputs of the light detecting components 3 and 4, which have been amplified by the amplifying units 20 and 21, the light transmittance of light having traveled the distance d within the lubricant 6 is detected and, hence, it is possible to estimate from the value of the detected output the amount of the alien substance admixed into the lubricant 6. Also, since an increase of the amount of the alien substance admixed means a progress of deterioration taking place in the lubricant 6, the determining unit 5 can detect the status of deterioration of the lubricant 6 from the amount of the alien substance estimated.

It is to be noted that the determining unit 5 may be of a type capable of determining the difference between the respective signal strengths of the outputs of the two light detecting components 3 and 4 which have been amplified by the amplifying units 20 and 21. Even in this case, the determining unit detects the light transmittance of rays of light transmitted the distance d within the lubricant 6 and, accordingly, the amount of the alien substance admixed into the lubricant 6 can be estimated from the detected output thereof and the status of deterioration of the lubricant 6 can accordingly detected from the amount of the alien substances so estimated.

In this lubricant deterioration detecting device 1, in the case where, for example, the thickness of the lubricant 6 is so small, the light transmittance is so large, the intensity of the light source 2 is so large, or the distance from the light source 2 to the light detecting component 3 is so small that the output of the light detecting component 3 may represent a value exceeding the value within the predetermined range, the gain adjusting unit 24 lowers the gain of the amplifying unit 20. Accordingly, the output of the light detecting component 3 amplified by the amplifying unit 20 can be adjusted to attain the value within the predetermined range and is then supplied to the determining unit 5 as an output for comparison purpose. The determining unit 5 compares the output of the light detecting component 3 so adjusted in the way described above, and the value of the output of the other light detecting component 4 amplified by the amplifying unit 21 with each other to thereby detect the light transmittance of the light traveling the distance d in the lubricant 6 (the status of deterioration of the lubricant 6). In such case, during the detection process taking place in the determining unit 5, the change of the gain effected by the amplifying unit 20 is taken into consideration.

Also, it may occur that depending on the thickness of the lubricant, the light transmittance, the intensity of the light source 2, or the distance from the light source 2 to the light detecting components 3 and 4, the output of the light detecting component 3 may represent a value exceeding the value within the predetermined range and, on the other hand, the output of the other light detecting component 4 may represent a value lower than the value within the predetermined range. In such case, not only does the gain adjusting unit 24 lower the gain of the amplifying unit 20, but the gain adjusting unit 25 increases the gain of the amplifying unit 21. Accordingly, the output of the light detecting component 3 amplified by the amplifying unit 20 and the output of the light detecting component 4 amplified by the amplifying unit 21 are adjusted to represent the respective values falling within the predetermined ranges and are then supplied to the determining unit 5 for comparison purpose. The determining unit 5 then compares the respective amplified outputs of the light detecting components 3 and 4 with each other to thereby detect the light transmittance of the light traveling the distance d in the lubricant 6 (the status of deterioration of the lubricant 6). In such case, during the detection process taking place in the determining unit 5, the change of the gains effected by the amplifying units 20 and 21, respectively, are taken into consideration.

As hereinabove described, in this lubricant deterioration detecting device 1, the two light detecting components 3 and 4 are so arranged that their light detecting faces are held displaced the distance d from each other relative to the direction of travel of the rays of light, and the respective outputs of those two light detecting components 3 and 4 are, after having been amplified by the amplifying units 20 and 21, compared with each other by the determining unit 5 to thereby detect the status of deterioration of the lubricant 6. Also, the gain adjusting units 24 and 25 automatically adjust the respective gains of the amplifying units 20 and 21 so that the outputs of the light detecting components 3 and 4 amplified by the amplifying units 20 and 21, respectively, can represent values within the predetermined range. For these reasons, the status of deterioration can be stably detected without being adversely affected by the thickness of the lubricant 6 itself, the light transmittance thereof, the intensity of the light source 2 and/or the distance from the light source 2 to the light detecting components 3 and 4.

As a result, even when the lubricant deterioration detecting device 1 is incorporated in, for example, the bearing assembly or the like, the degree of freedom of arrangement comes to be high and construction is possible to accommodate to the limited available space for installation. Also, considering that the status of deterioration of the lubricant 6 is detected by comparing the respective outputs of the light detecting components 3 and 4, a stable detection can be accomplished without being adversely affected by common mode noises such as a power source variation. In addition, since the light detecting components 3 and 4 are arranged within the lubricant 6, influences brought about by a temperature dependent change in characteristic of those two light detecting components 3 and 4 can be counterbalanced and, accordingly, a highly accurate detection can be accomplished.

It is to be noted that in the construction described above, arrangement may be made that the result of detection can be made based on a change in temperature by disposing a temperature sensor in proximity of the light detecting components 3 and 4 for monitoring the temperatures of the lubricant 6 and the light detecting components 3 and 4. More specifically, for example, a circuit may be employed for correcting the detection signal generated at the temperature measured at the time of actual use, if a change in detection signal with change in temperature is beforehand measured. In such case, by sensing the temperature of the lubricant 6, it is possible to avoid the possibility that a change in detection signal with change in ambient temperature would be erroneously determined as resulting from deterioration of the lubricant 6. In this way, an accurate detection can be accomplished.

When this lubricant deterioration detecting device 1 to be operated, the amplifying units 20 and 21 may be used in the following manner depending on the signal strengths of the outputs of the light detecting components 3 and 4.

1. When the respective outputs of the light detecting components 3 and 4 are both low, those outputs of the light detecting components 3 and 4 are amplified by the respective amplifying units 20 and 21.
2. When only the output of the light detecting component 4 is low, only this output is amplified by the associated amplifying units 20 and 21. In such case, depending on the necessity, the output of the light detecting component 3 may be attenuated by the amplifying unit 21.
3. The gains are to be set to such proper values that the respective outputs of the amplifying units 20 and 21 may become the same and, by comparing the values of those gains, the light transmittance of the lubricant 6 (the status of deterioration thereof) is to be estimated.

Figure 17:
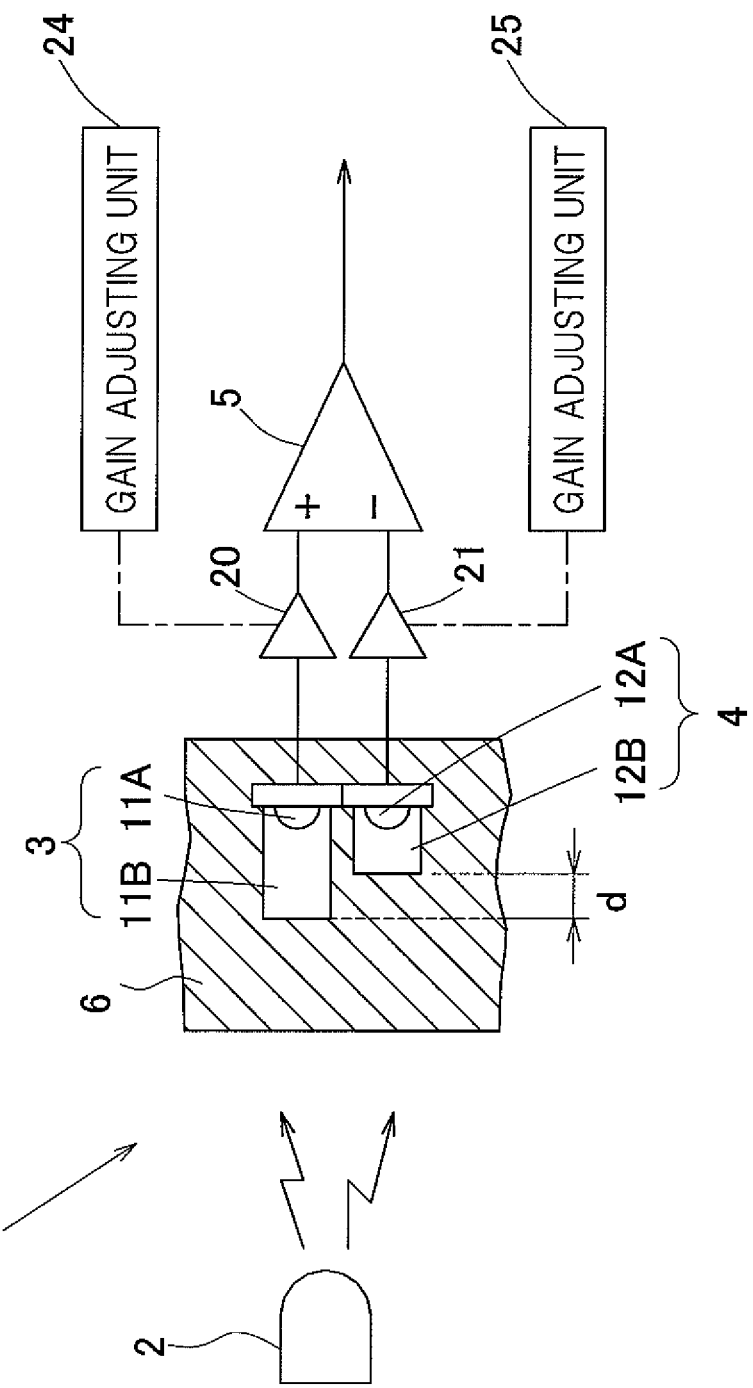
FIG. 17 is a schematic structural diagram showing the lubricant deterioration detecting device according to a tenth preferred embodiment of the present invention.

FIG. 17 illustrates a schematic structural diagram showing a tenth preferred embodiment of the present invention. This lubricant deterioration detecting device 1 according to this embodiment is similar to that according to the ninth embodiment shown in and described with reference to FIG. 12, but differs therefrom in that each of the light detecting components 3 and 4 includes a detector 11A and 12A and a light guide element 11B and 12B. More specifically, the light guide element 3 is made up of the detector 11A and the light guide element 11B having a base end connected with the detector 11A and a free end defining a light detecting face, while the light detecting component 4 is made up of the detector 12A and the light guide element 12B having a base end connected with the detector 12A and a free end defining a light detecting face. For each of the detectors 11A and 12A, a photodiode, a phototransistor, a CDS, a solar cell or a photomultiplier may be employed. In this case, the two detectors 11A and 12A are juxtaposed at the same position relative to the direction of travel of the rays of light. In contrast thereto, the two light guide elements 11B and 12B have respective varying lengths so that their free ends are held displaced the predetermined distance d from each other relative to the direction of travel of the rays of light. Accordingly, the respective positions of the light detecting faces of those two light detecting components 3 and 4 are displaced the predetermined distance d from each other relative to the direction of travel of the rays of light. Each of the light guide elements 11B and 12B is made of a transparent material such as, for example, a cylindrical synthetic resin or glass and the free end thereof, which defines the light detecting face, represents a transparent round window, and an outer peripheral surface of each of the light guide elements 11B and 12B is coated with a reflective material. It is to be noted that each of the light guide elements 11B and 12B may not be always limited to that having a cylindrical shape, but may have a rectangular sectioned tubular shape. Other structural features than those described above are similar to those employed in the ninth embodiment.

Even in the case of the lubricant deterioration detecting device 1, since the two light detecting components 3 and 4 are so arranged as to have their light detecting faces held displaced the distance d from each other relative to the direction of travel of the rays of light, the status of deterioration of the lubricant 6 can be detected without being adversely affected by thickness or light transmittance of the lubricant 6 itself, the intensity of the light source 2 and/or the distance from the light source to the light detecting components 3 and 4.

Figure 18:
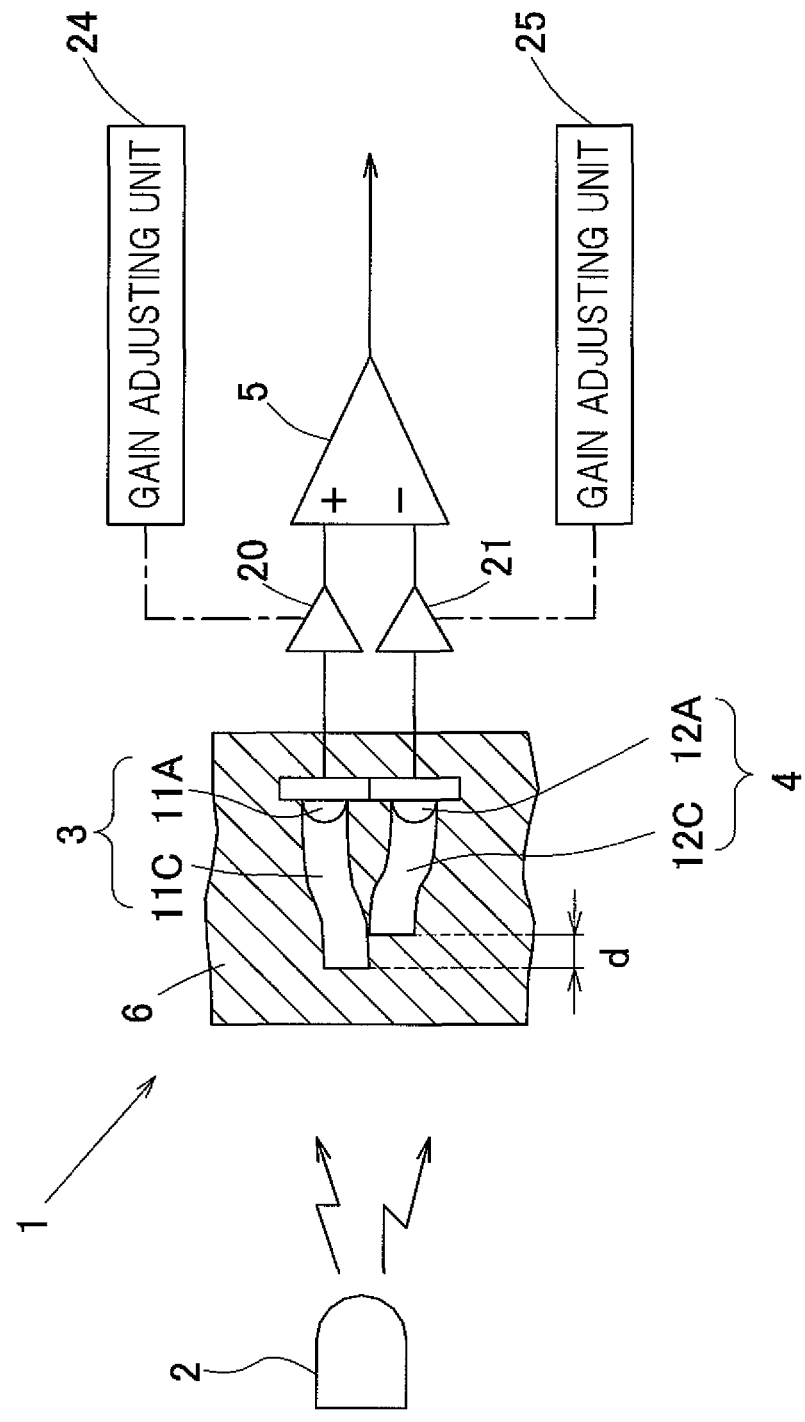
FIG. 18 is a schematic structural diagram showing the lubricant deterioration detecting device according to an eleventh preferred embodiment of the present invention.

FIG. 18 illustrates a schematic structural diagram showing an eleventh preferred embodiment of the present invention. The lubricant deterioration detecting device 1 according to this embodiment is similar to that according to the ninth embodiment shown in and described with reference to FIG. 12, but differs therefrom in that each of the two light detecting components 3 and 4 is made up of a detector 11A and 12A and an optical fiber 11C and 12C. In other words, the light detecting component 3 is made up of the detector 11A and the optical fiber 11C having a base end connected with the detector 11A and a free end defining the light detecting face, while the light detecting component 4 is made up of the detector 12A and the optical fiber 12C having a base end connected with the detector 12A and a free end defining the light detecting face. For each of the detectors 11A and 12A, a photodiode, a phototransistor, a CDS, a solar cell or a photomultiplier may be employed. Even in this case, the two detectors 11A and 12A are juxtaposed at the same position relative to the direction of travel of the rays of light and the two optical fibers 11C and 12C have respective lengths so that their free ends are held displaced the predetermined distance d from each other relative to the direction of travel of the rays of light. Accordingly, the respective positions of the light detecting faces of those two light detecting components 3 and 4 are displaced the predetermined distance d from each other relative to the direction of travel of the rays of light. Other structural features than those described above are similar to those employed in the ninth embodiment.

Even in the case of the lubricant deterioration detecting device 1, since the two light detecting components 3 and 4 are so arranged as to have their light detecting faces held displaced the distance d from each other relative to the direction of travel of the rays of light, the status of deterioration of the lubricant 6 can be detected without being adversely affected by thickness or light transmittance of the lubricant 6 itself, the intensity of the light source 2 and/or the distance from the light source to the light detecting components 3 and 4.

Figure 19:
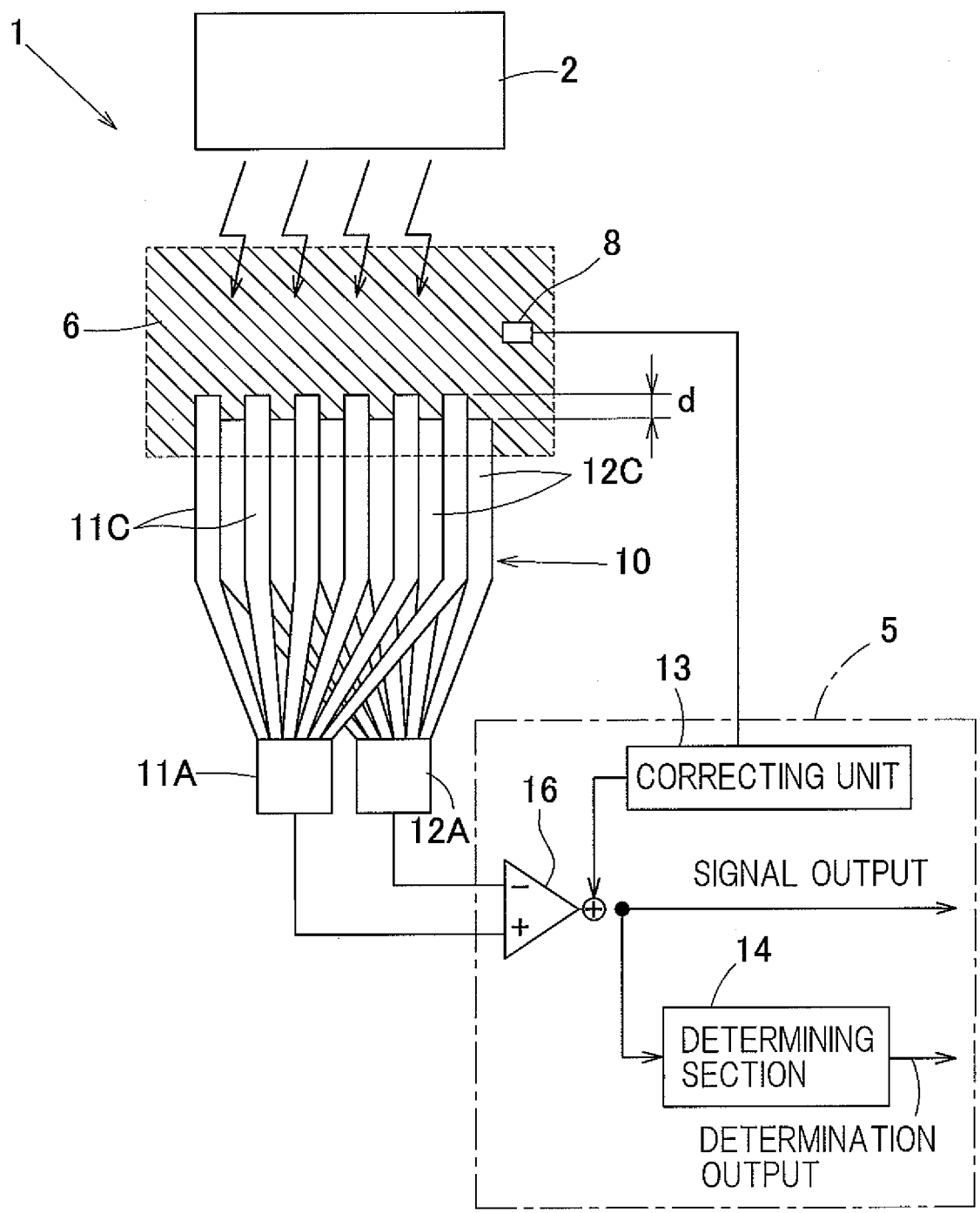
FIG. 19 is a schematic structural diagram showing the lubricant deterioration detecting device which is a lubricant deterioration detecting device according to a twelfth preferred embodiment of the present invention.

A twelfth preferred embodiment of the present invention will be described with particular reference to FIGS. 19 to 21. FIG. 19 illustrates a schematic structural diagram of the lubricant deterioration detecting device according to this embodiment. This lubricant deterioration detecting device 1 includes a bundled optical fiber array 10 made up of two bundles of optical fibers 11C and 12C which have their free ends displaced a predetermined distance d from each other, detectors 11A and 12A connected with base end of the optical fiber bundle 11C and base end of the optical fiber bundle 12C, respectively, a light source 2 positioned at a location confronting a free end of the bundled optical fiber array 10, and a comparing unit 5 for comparing signal outputs of the two detectors 11A and 12A to measure the light transmittance of the lubricant 6. A position proximate to the free end of the bundled optical fiber array 10 and adjacent the light source 2 is chosen to be a site of the lubricant 6 and respective free ends of the optical fibers 11C and 12C, which define their light detecting faces, are held within the lubricant 6.

It is to be noted that a temperature sensor 8 is provided in proximity of the free end of the bundled optical fiber array 10. Each of the bundles of optical fibers 11C and 12C is made up of a plurality of optical fibers, and a total light receiving surface area of one of the bundles of optical fibers 11C is chosen to be equal to that of the other of the bundles of optical fibers 12C. Except that the bundles of optical fibers 11C and 12C have respective free ends displaced from each other and also have respective base ends confronting the different detectors 11A and 12A, they are of the same construction.

For the light source 2, an LED, an incandescent bulb, a semiconductor laser diode, an EL, an organic EL or a fluorescent tube may be employed. Also, for each of the detectors 3 and 4, a photodiode, a phototransistor, a CDS, a solar cell or a photomultiplier may be employed. In FIG. 19, the determining unit 5 is shown as including a differential amplifier 16 for determining the difference between the respective signal strengths of the output of the detectors 11A and 12A, respectively, a determining section 14 for comparing a signal output of this differential amplifier 16 with a reference value, and a correcting unit 13 for correcting an output of the determining unit 5 in reference to a detected value of the temperature sensor 8, but the present invention may not be always limited thereto and the determining unit 5 may have a circuit configuration operable to determine the ratio between the signal strengths of the outputs of those two detectors 11A and 12A.

Also, the constant α in the equation (4) described previously varies depending on the status of the lubricant 6. By way of example, where the lubricant 6 is of a kind filled in the bearing assembly, foreign matter such as, for example, powdery wear debris are admixed into the lubricant 6 as the bearing assembly is used in practice and, accordingly, the constant α increases with an increase of the amount of the alien substance admixed. Also, oxidization and discoloring occur as deterioration of the lubricant proceeds and, therefore, where the lubricant 6 is a lubricating agent, the constant α increases as the lubricating agent is deteriorated. Accordingly, where the determining unit 5 determines the ratio between the signal strengths of the two detectors 11A and 12A, the light transmittance of light traveling the optical distance d in the lubricant 6 is measured and, therefore, based on the value of the detected output, the amount of the alien substance admixed in the lubricant can be estimated or the status of deterioration of the lubricant can be detected.

Even where in the determining unit 5, the difference between the respective signal strengths of the two detectors 11A and 12A is determined by means of the differential amplifier 16 as is the case with FIG. 19, the light transmittance of the light traveling the optical distance d in the lubricant 6 is measured. For this reason, based on the detected output, the amount of the alien substance admixed in the lubricant can be estimated or the status of deterioration of the lubricant can be detected.

As hereinabove described, this lubricant deterioration detecting device 1 is so designed that a bundled optical fiber array 10 is provided, which is made up of two bundles of optical fibers 11C and 12C having their free ends displaced a predetermined distance d from each other, in combination with the two detectors 11A and 12A connected with base ends of the optical fiber bundle 11C and base end of the optical fiber bundle 12C, respectively, also with the light source 2 positioned at a location confronting a free end of the bundled optical fiber array 10, while a position proximate to the free end of the bundled optical fiber array 10 and adjacent the light source 2 is chosen to be the site of the lubricant 6 so that the transmittance of the lubricant 6 can be measured by comparing, with the determining unit 5. Accordingly, the light transmittance of a lubricant 6 can be stably and accurately measured without being adversely affected by the thickness of the lubricant 6 itself the amount of the lubricant 6, the intensity of the light source 2 and the distance from the light source 2 to the detectors 11A and 12A. As a result thereof, even when the lubricant deterioration detecting device 1 is incorporated in, for example, the bearing assembly or the like, the degree of freedom of arrangement comes to be high and construction is possible to accommodate to the limited available space for installation. Also, considering that the light transmittance of the lubricant 6 is detected by comparing the respective signal outputs of the detectors 11A and 12A, a stable detection can be accomplished without being adversely affected by common mode noises such as a power source variation. In addition, since the bundled optical fiber array 10 is employed, a sufficient light receiving surface area can be secured on the light receiving side. For this reason, not only can a sufficient light receiving strength can be obtained with the detectors 11A and 12A, but any variation in thickness of the lubricant 6 brought about by the position can be cancelled and, therefore, a stable measurement of the light transmittance can be accomplished.

Also, with the determining unit 5 shown in FIG. 19, since the temperature sensor 8 disposed in proximity of the free end of the bundled optical fiber array 10 detects the temperature of the lubricant 6 and the detectors 11A, 12A to thereby measure the temperature dependent characteristic of the lubricant based on the detected value thereof, or apply the correction appropriate to the change in temperature by the correcting unit 13 to the result of measurement based on the detected value thereof. Accordingly, it is possible to avoid the possibility that a change in measured value resulting from change of the ambient temperature would be erroneously determined as having resulted from the deterioration of the lubricating agent which is the lubricant 6. In this way, a further accurate measurement can be accomplished.

In addition, with the determining unit 5 shown in FIG. 19, since the provision is made of the determining unit 14 for comparing the detection signal, which can be obtained by comparing the respective signal output of the two detectors 11A and 12A, respectively, with each other, with the predetermined reference value, it can readily determined that the status of deterioration of, for example, a lubricating agent which is the lubricant 6, is above a predetermined level and, thus, it can be used as an indication of the time of replacement.

Figure 20:
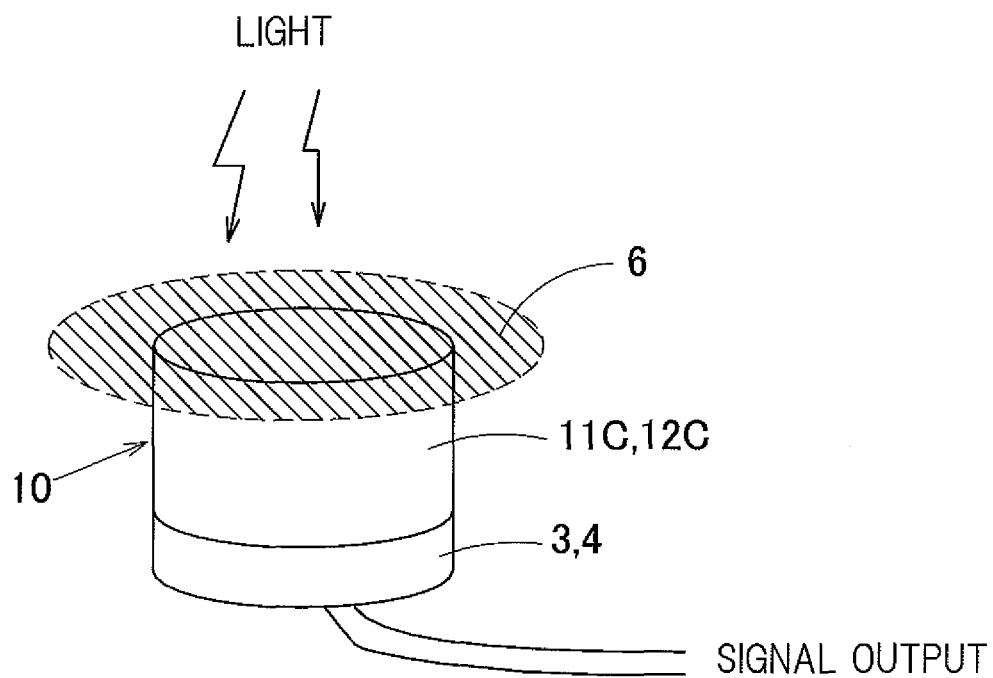
FIG. 20 is a perspective showing a specific structural example of a light receiving side of the lubricant deterioration detecting device.

FIG. 20 illustrates a specific constructional example of the light receiving side of the lubricant deterioration detecting device 1 shown in FIG. 19. In this example, the two bundles of optical fibers 11C and 12C forming the bundled optical fiber array 10 are so bundled together that a free end thereof, which define the light detecting face, may represent a planar shape, for example, a round shape.

Where the free end of the bundled optical fiber array 10 is planarly arranged to represent a planar shape, averaging can be made even though the distribution of thickness of the lubricant 6 varies and, therefore, a stable measurement can be accomplished without such variation adversely affecting the measured value. Also, merely positioning of the light source 2 (in FIG. 19) in face-to-face relation with the bundled optical fiber array 10 having the lubricant 6 deposited on the free end face thereof makes it possible to accomplish the stable measurement. It is to be noted that in such case, it is preferable to increase the surface area of the light source 2 to suit to the light receiving surface area of the bundled optical fiber array 10 or to employ the light source 2 in the form of a planar light emitting body.

Figure 21:
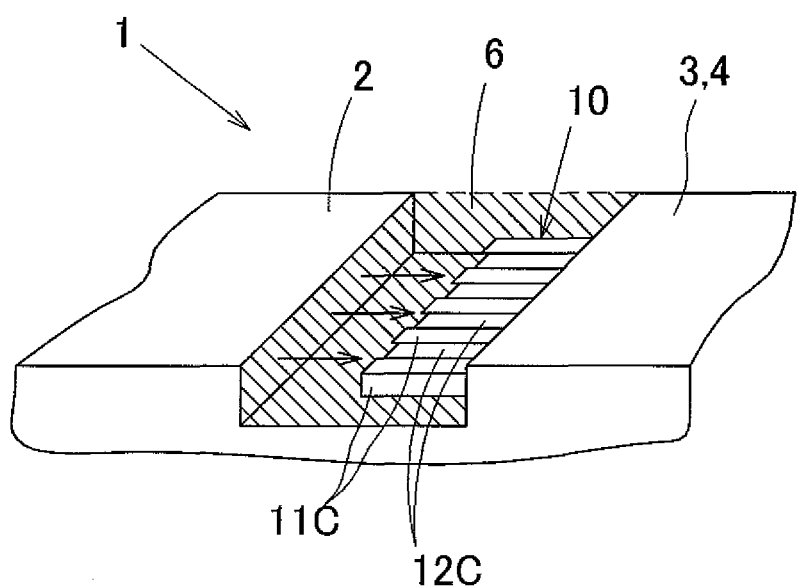
FIG. 21 is a perspective view showing another specific structural example of the lubricant deterioration detecting device.

FIG. 21 illustrates another specific constructional example of the lubricant deterioration detecting device 1 shown in FIG. 19. In this example, the two bundles of optical fibers 11C and 12C forming the bundled optical fiber array 10 are arranged in line.

Where the two bundles of optical fibers 11C and 12C are arranged in line as described above, the light receiving unit can be constructed to have a thin structure and, therefore, the light transmittance of a lubricant 6 distributed in a planar shape can be measured. It is to be noted that even in this case, it is preferable to employ the light source 5 in the form having a linear shape so that the light receiving efficiency can be increased.

Figure 22:
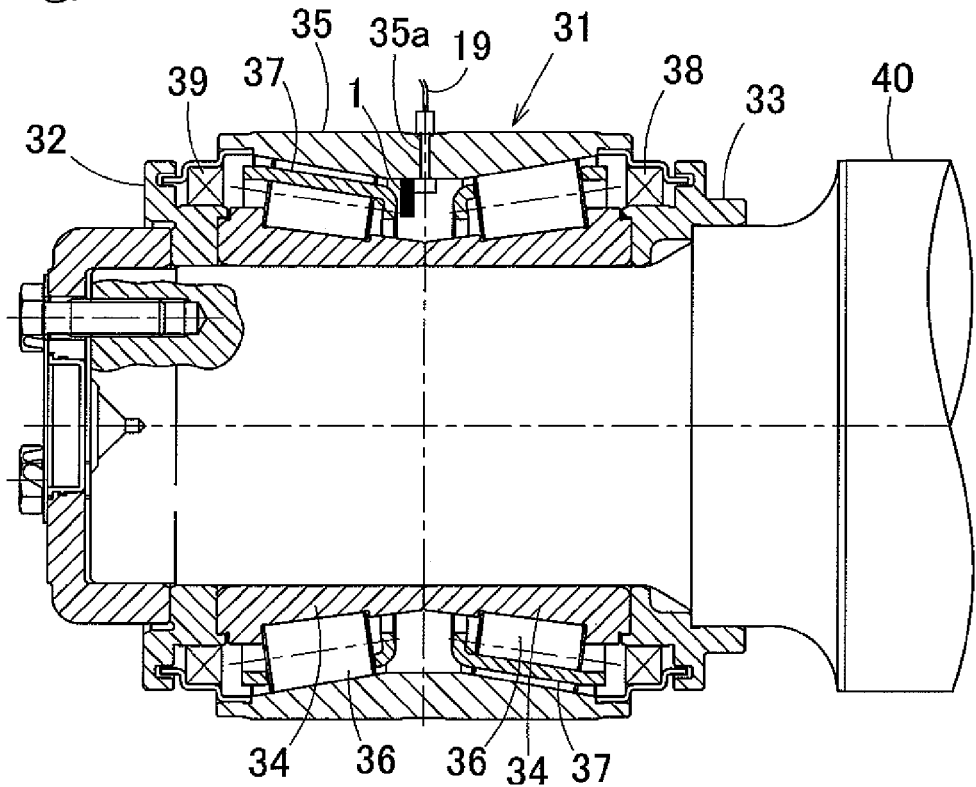
FIG. 22 is a sectional view showing an example of a lubricant deterioration detector incorporated bearing assembly equipped with the lubricant deterioration detecting device referred to above.

FIG. 22 illustrates a sectional view showing a detecting device incorporated bearing assembly having the lubricant detection detecting device 1 of the structure described hereinabove, which is used in a railway vehicle bearing part. The railway vehicle bearing unit in this case includes a detecting device incorporated bearing assembly 31, and an oil slinger 32 and a rear lid 33, which are accessory components that are provided in contact with opposite ends of an inner ring 34. The bearing assembly 31 is in the form of a rolling bearing, more specifically a double row tapered roller bearing and includes split type inner rings 34 and 34, each provided for a row of rolling elements 36, an unitary outer ring 35, rows of rolling elements 36 and 36 and retainers 37.

The rear lid 33 is mounted on a wheel axle 40 at a location closer to the midpoint thereof than the location of the bearing assembly 31 and has an outer periphery with which an oil seal 38 is slidingly engaged. The oil slinger 32 is mounted on the wheel axle 40 and has an outer periphery with which an oil seal 39 is slidingly engaged. The oil seals 38 and 39 arranged on opposite ends of the bearing assembly 31 serve to seal the lubricant within the bearing assembly 31 and, accordingly, the dust proofing and the resistance to water can be secured.

The lubricant deterioration detecting device 1 is fitted intermediate between the rows of raceway surfaces defined in the inner diametric surface of an outer ring 35 of the bearing device 31 for detecting the status of deterioration of the lubricant sealed within the bearing unit. The lubricant deterioration detecting device 1 is arranged in proximity to end faces of the rollers 36. The outer ring 35 is formed with a cable insertion hole 35a for passage therethrough of a wiring cable 19 of the lubricant deterioration detecting device 1, and a portion where the wiring cable 19 is inserted is treated to have a water resistance and an oil resistance. Through the wiring cable 19, an electric power supply from outside of the bearing to the lubricant deterioration detecting device 1 and transmission of the detection signal to outside of the bearing is carried out. In this way, any ingress of water and/or dusts into the bearing unit through an area where the lubricant deterioration detecting device 31 is fitted can be avoided.

In the detecting device incorporated bearing assembly 31 having the above described lubricant deterioration detecting device 1 mounted thereon, deterioration of the lubricant filled within the bearing unit can be accurately detected in real time or regularly. As a result, prior to an actual occurrence of an abnormality in the bearing device 31, the necessity of replacement of the lubricant can be judged and it is possible to prevent the bearing device 31 from being damaged as a result of the defective lubricant. Also, since the necessity of replacement of the lubricant can be determined in reference to the output of the lubricant deterioration detecting device 1, the amount of the lubricant which may be discarded prior to the life time of use can be reduced.

Figure 23:
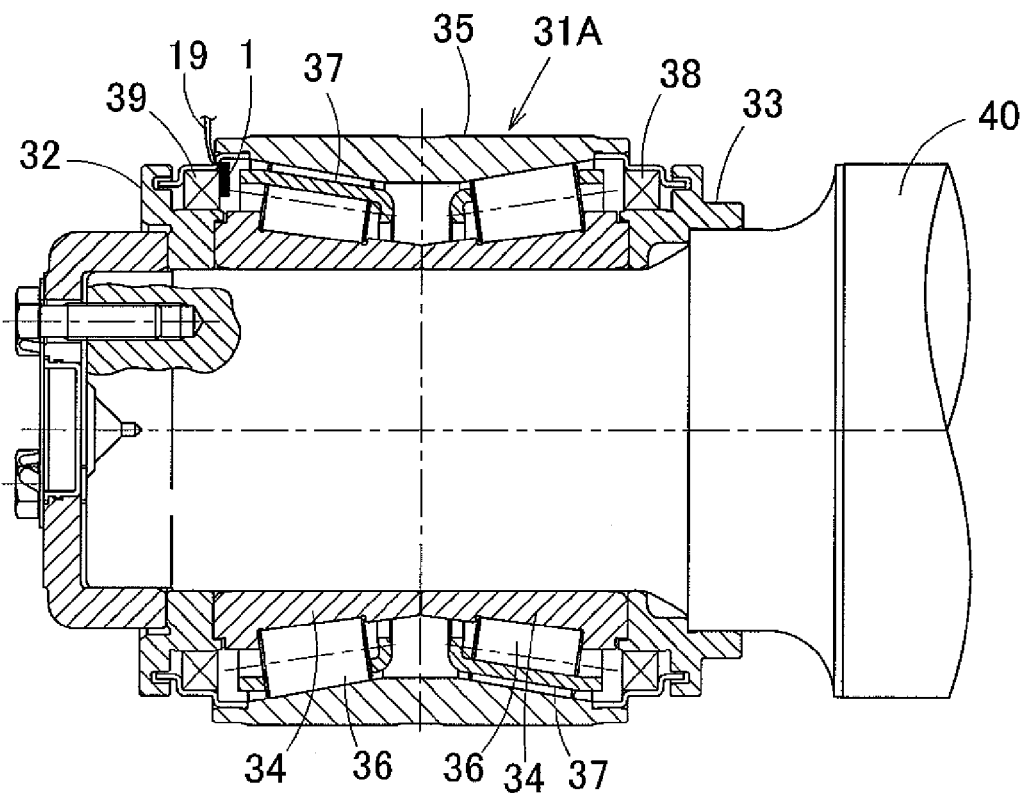
FIG. 23 is a sectional view showing another example of the lubricant deterioration detector incorporated bearing assembly equipped with the lubricant deterioration detecting device referred to above.

FIG. 23 illustrates another example of the detecting device incorporated bearing assembly. This detecting device incorporated bearing assembly 31A is similar to the detecting device incorporated bearing assembly 31 shown in and described with reference to FIG. 22, but differs therefrom in that the lubricant deterioration detecting device 1 is fitted to an inner surface of the oil seal 39. In such case, the lubricant deterioration detecting device 1 is arranged proximate to an end face of the retainer 37.

Figure 24:
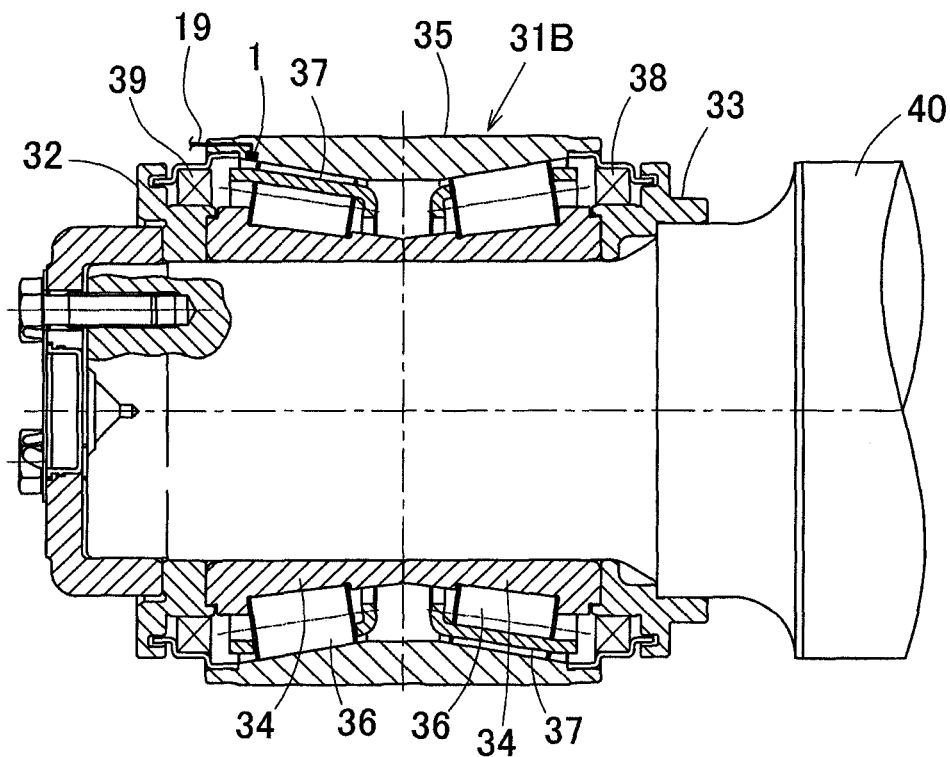
FIG. 24 is a sectional view showing a further example of a lubricant deterioration detector incorporated bearing assembly equipped with the lubricant deterioration detecting device referred to above.
Figure 25:
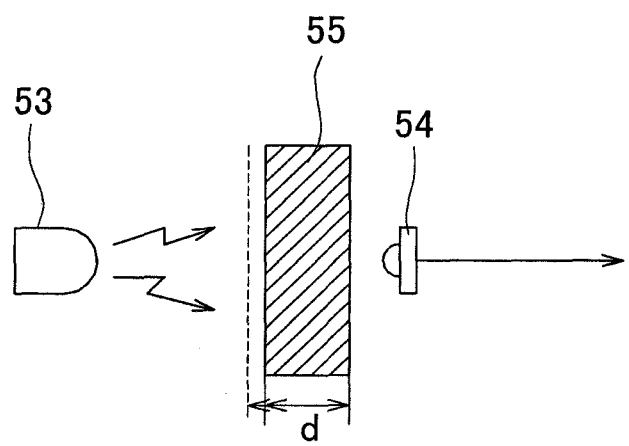
FIG. 25 is a schematic structural diagram showing the suggested example of the lubricant deterioration detecting device.
Figure 26:
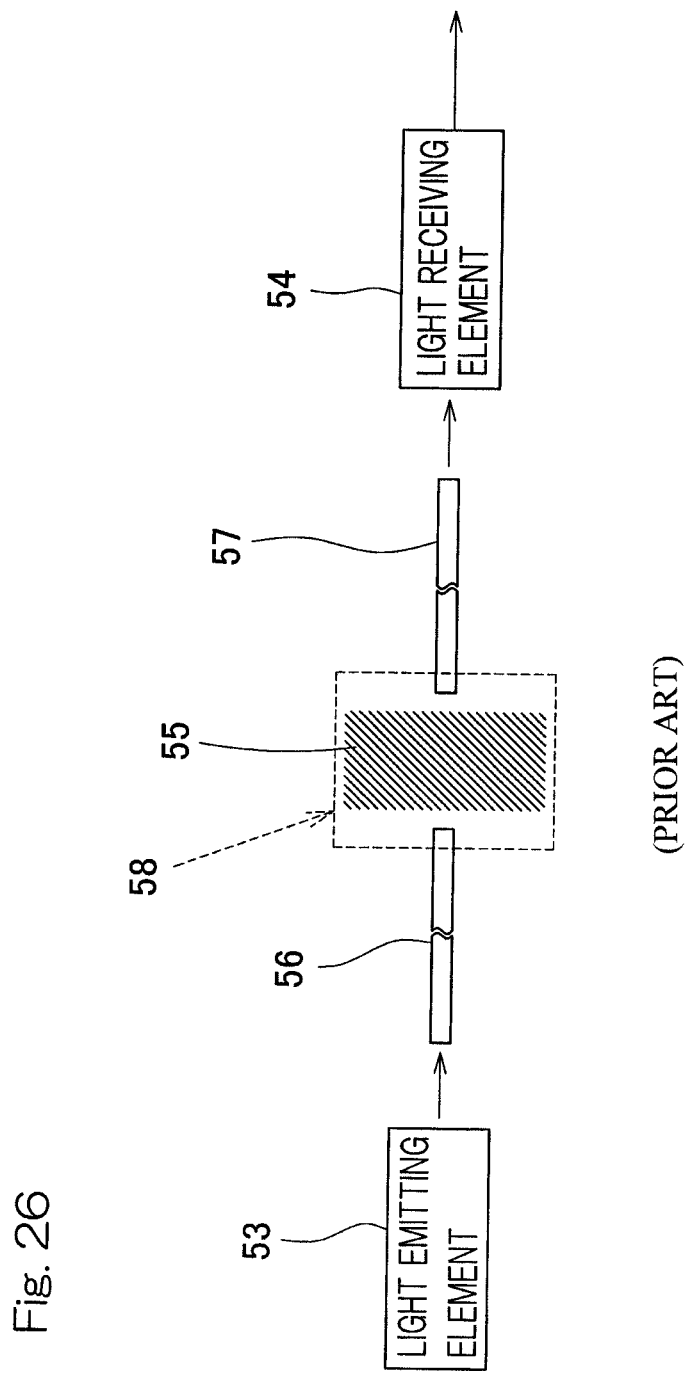
FIG. 26 is a schematic structural diagram showing the different suggested example of the lubricant deterioration detecting device.

FIG. 24 illustrates a further example of the detecting device incorporated bearing assembly. This detecting device incorporated bearing assembly 31B is similar to the detecting device incorporated bearing assembly 31 shown in and described with reference to FIG. 22, but differs therefrom in that the lubricant deterioration detecting device 1 is fitted to one side of the raceway surface of the outer ring 35. Positioning of the lubricant deterioration detecting device 1 on one side of the raceway surface as hereinabove described is effective to assuredly detect the status of the lubricant then attributing to lubrication.

Hereinafter, a transmittance detecting device, which is an applied technology different in basic structure from the present invention will now be described.

The transmittance detecting device referred to above is so designed as to include a bundled optical fiber array made up of two bundles of optical fibers having their free end displaced relative to each other, with base ends of the optical fibers of the bundled optical fiber array connected with two light detectors one employed for each of the two bundles of optical fibers, a light source positioned in face-to-face relation with a free end of the bundled optical fiber array, and a determining unit for measuring the light transmittance of a sample by comparing signal outputs from the two light detectors, wherein a position adjacent the light source proximate to the free end of the bundled optical fiber array is chosen to be an area of placement of the sample.

In other words, the lubricant deterioration detecting device shown in and described with reference to FIG. 19 is applied as an apparatus for detecting the transmittance of any other sample than the lubricant.

According to this construction, the amount of light attenuated after having passed across the thickness of the sample, which corresponds to the displacement in position of the free ends of the two bundles of optical fibers can be detected by comparison of the signal outputs from the two detectors. For this reason, without being adversely affected by the thickness of the sample itself, the amount of the sample, the intensity of the light source and the distance from the light source to the light detectors, the light transmittance of the sample can be stably and accurately detected. As a result thereof, even when the transmittance detecting device is incorporated in, for example, the bearing assembly or the like, the degree of freedom of arrangement comes to be high and construction is possible to accommodate to the limited available space for installation. Also, considering that the status of deterioration of the lubricant 6 is detected by comparing the respective signal outputs of the light detectors, a stable detection can be accomplished without being adversely affected by common mode noises such as a power source variation. In addition, since the optical fibers are employed and since a sufficient light receiving surface area can be secured on the light receiving side, not only can the intensity of received light be obtained with the light detectors, but also any variation in thickness of the sample depending on the position can be cancelled and, hence, even in this respect, the light transmittance can be stably measured.

What is claimed is:

1. A lubricant deterioration detecting device which comprises:
   a single light source having linear shape;
   a plurality of light detecting components, arranged in line in correspondence with the linear shape of the light source, for detecting rays of light emitted from the light source and subsequently transmitted through a lubricant, wherein
      each of the plurality of light detecting components includes only a single detector and only a single light guide element having one end in the form of a base end connected with the detector and the other end in the form of a free end forming a light detecting face,
      each of the light detecting faces faces a same direction of travel of the rays of light, and
      the light guide elements have respective lengths different from each other so that the light detecting faces are sequentially displaced in position by a distance relative to the direction of travel of rays of light; and
   a determining unit operable to compare respective signal strengths of outputs from the detectors connected respectively with the light guide elements having respective lengths different from each other to thereby detect a status of deterioration of the lubricant,
   wherein the lubricant deterioration detecting device is provided within a bearing assembly for detecting a status of deterioration of a lubricant filled within the bearing assembly.

2. The lubricant deterioration detecting device as claimed in claim 1, wherein the determining unit is of a type capable of estimating an amount of an alien substance admixed into the lubricant through comparison of the signal strengths.

3. The lubricant deterioration detecting device as claimed in claim 1, wherein the light guide element of each of the light detecting components is in the form of an optical fiber.

4. The lubricant deterioration detecting device as claimed in claim 1, wherein the determining unit is of a type capable of calculating a light transmittance of the lubricant.

5. The lubricant deterioration detecting device as claimed in claim 1, wherein the determining unit includes a selector section for excluding, from the output signals of the plural light detecting components, output signals of a light detecting components which generate a saturated output, and output signals of light detecting components indicative of a detected light intensity not attaining a predetermined value, in order to use output signals of the rest of the light detecting components for detection of the status of deterioration of the lubricant.

6. The lubricant deterioration detecting device as claimed in claim 1, which includes two light detecting components.

7. The lubricant deterioration detecting device as claimed in claim 6, further comprising a temperature sensor positioned in proximity to the light detecting components.

8. The lubricant deterioration detecting device as claimed in claim 6, further comprising a light amount adjusting unit for adjusting an amount of light of the light source so that an output of one of the two light detecting components, which is closest to the light source, attains a predetermined constant value.

9. The lubricant deterioration detecting device as claimed in claim 6, further comprising a light amount adjusting unit for adjusting an amount of light of the light source so that an output of one of the two light detecting components, which is remotest from the light source, attains a predetermined constant value.

10. The lubricant deterioration detecting device as claimed in claim 6, further comprising an amplifying unit for amplifying an output of each of the light detecting components and a unit for adjusting a gain of the amplifying unit, wherein the determining unit compares the outputs amplified by the amplifying unit to detect the status of deterioration of the lubricant, and wherein the gain adjusting unit adjusts a gain of the amplifying unit to allow the output of each of the light detecting components, which has been amplified by the amplifying unit, to attain a value within a predetermined range.

11. The lubricant deterioration detecting device as claimed in claim 1 including two light detecting components, wherein each of the light detecting components includes a detector and a optical fiber bundle having one end in the form of a base end connected with a detector and the other end in the form of a free end forming a light detecting face.

12. The lubricant deterioration detecting device as claimed in claim 11, further comprising a temperature sensor positioned proximate to the free ends of the optical fiber bundles, and a correcting unit for correcting an output of the determining unit based on a detected value of the temperature sensor.

13. The lubricant deterioration detecting device as claimed in claim 11, wherein each of the respective free ends of the optical fiber bundles is arranged in line.

14. The lubricant deterioration detecting device as claimed in claim 13, wherein the light source is in the form of a linear-shaped light source corresponding to a line shaped arrangement of the free ends of the optical fiber bundles.

15. The lubricant deterioration detecting device as claimed in claim 11, wherein the optical fiber bundles have respective free end faces that are planarly arranged.

16. The lubricant deterioration detecting device as claimed in claim 15, wherein the light source is a planar light source corresponding to the planar shape in which the free ends of the optical fiber bundles are arranged.

17. A detecting device incorporated bearing assembly having a lubricant deterioration detecting device as defined in claim 1 provided in a bearing space delimited by oil seals arranged on opposite ends of the bearing assembly.

\* \* \* \* \*